United States Patent
Collins et al.

(10) Patent No.: US 10,303,641 B2
(45) Date of Patent: May 28, 2019

(54) AUTHENTICATION AND INFORMATION SYSTEM FOR REUSABLE SURGICAL INSTRUMENTS

(71) Applicant: Covidien LP, Mansfield, MA (US)

(72) Inventors: Ethan Collins, Naugatuck, CT (US); John Hryb, Southington, CT (US); David Durant, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/160,551

(22) Filed: Oct. 15, 2018

(65) Prior Publication Data

US 2019/0050364 A1 Feb. 14, 2019

Related U.S. Application Data

(63) Continuation of application No. 14/670,837, filed on Mar. 27, 2015.

(60) Provisional application No. 61/989,609, filed on May 7, 2014.

(51) Int. Cl.
| | |
|---|---|
| *G06F 13/42* | (2006.01) |
| *G06F 19/00* | (2018.01) |
| *G16H 40/63* | (2018.01) |
| *A61B 90/90* | (2016.01) |
| *A61B 17/072* | (2006.01) |
| *A61B 17/00* | (2006.01) |

(Continued)

(52) U.S. Cl.
CPC .... *G06F 13/4221* (2013.01); *A61B 17/07207* (2013.01); *A61B 90/90* (2016.02); *G06F 13/4282* (2013.01); *G06F 19/00* (2013.01); *G16H 40/63* (2018.01); *A61B 90/98* (2016.02); *A61B 2017/00017* (2013.01); *A61B 2017/0046* (2013.01); *A61B 2017/00398* (2013.01); *A61B 2090/064* (2016.02); *A61B 2090/0814* (2016.02); *Y02A 90/26* (2018.01)

(58) Field of Classification Search
None
See application file for complete search history.

(56) References Cited

U.S. PATENT DOCUMENTS

| | | |
|---|---|---|
| 4,660,818 A | 4/1987 | Conner et al. |
| 6,298,255 B1 | 10/2001 | Cordero et al. |

(Continued)

FOREIGN PATENT DOCUMENTS

| | | |
|---|---|---|
| CA | 2104423 A1 | 2/1994 |
| CA | 2520413 A1 | 3/2007 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner* — Idriss N Alrobaye
*Assistant Examiner* — Dayton Lewis-Taylor

(57) ABSTRACT

An authentication and information system for use in a surgical stapling system includes a microprocessor configured to demultiplex data from a plurality of components in the surgical system. The authentication and information system can include one wire chips and a coupling assembly with a communication connection.

20 Claims, 33 Drawing Sheets

(51) Int. Cl.
 *A61B 90/00* (2016.01)
 *A61B 90/98* (2016.01)

(56) References Cited

U.S. PATENT DOCUMENTS

| | | | | |
|---|---|---|---|---|
| 6,356,536 | B1 * | 3/2002 | Repke | H04B 1/48 370/282 |
| 6,608,571 | B1 | 8/2003 | Delvaux | |
| 6,708,049 | B1 | 3/2004 | Berson et al. | |
| 7,273,483 | B2 | 9/2007 | Wiener et al. | |
| 8,968,276 | B2 | 3/2015 | Zemlok et al. | |
| 2008/0185419 | A1 * | 8/2008 | Smith | A61B 17/1114 227/179.1 |
| 2010/0017553 | A1 | 1/2010 | Laurencin et al. | |
| 2010/0069898 | A1 | 3/2010 | O'Neil et al. | |
| 2011/0062211 | A1 | 3/2011 | Ross et al. | |
| 2014/0012289 | A1 | 1/2014 | Snow et al. | |
| 2015/0351765 | A1 * | 12/2015 | Valentine | A61B 17/07207 227/176.1 |

FOREIGN PATENT DOCUMENTS

| | | |
|---|---|---|
| CA | 2590520 A1 | 11/2007 |
| CN | 201299462 Y | 9/2009 |
| DE | 2415263 A1 | 10/1975 |
| DE | 02514501 A1 | 10/1976 |
| DE | 2627679 A1 | 1/1977 |
| DE | 03423356 A1 | 1/1986 |
| DE | 3612646 A1 | 4/1987 |
| DE | 8712328 U1 | 3/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102004026179 B4 | 1/2009 |
| DE | 102008018406 B3 | 7/2009 |
| EP | 0364216 A1 | 4/1990 |
| EP | 0467501 A1 | 1/1992 |
| EP | 0480293 A1 | 4/1992 |
| EP | 0509670 A3 | 12/1992 |
| EP | 0306123 B1 | 8/1993 |
| EP | 0569600 A1 | 11/1993 |
| EP | 0572131 A1 | 12/1993 |
| EP | 0584787 A1 | 3/1994 |
| EP | 0589555 A1 | 3/1994 |
| EP | 0589453 A3 | 4/1994 |
| EP | 0648475 A1 | 4/1995 |
| EP | 0624348 A3 | 6/1995 |
| EP | 0518230 B2 | 5/1996 |
| EP | 0741996 A2 | 11/1996 |
| EP | 0517243 B1 | 9/1997 |
| EP | 0541930 B1 | 3/1998 |
| EP | 0878169 A1 | 11/1998 |
| EP | 0623316 B1 | 3/1999 |
| EP | 0650701 B1 | 3/1999 |
| EP | 0923907 A1 | 6/1999 |
| EP | 0640317 B1 | 9/1999 |
| EP | 0947167 A1 | 10/1999 |
| EP | 0950378 A1 | 10/1999 |
| EP | 0986990 A1 | 3/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1177771 A1 | 2/2002 |
| EP | 1186274 A2 | 3/2002 |
| EP | 1278007 | 1/2003 |
| EP | 1281878 A1 | 2/2003 |
| EP | 1159926 A2 | 3/2003 |
| EP | 0717966 B1 | 4/2003 |
| EP | 1301135 A1 | 4/2003 |
| EP | 0887046 B1 | 7/2003 |
| EP | 1330991 | 7/2003 |
| EP | 0913126 B1 | 10/2004 |
| EP | 1472984 A1 | 11/2004 |
| EP | 0754437 B2 | 12/2004 |
| EP | 0888747 B1 | 12/2004 |
| EP | 1025807 B1 | 12/2004 |
| EP | 1486177 A2 | 12/2004 |
| EP | 0774232 B1 | 1/2005 |
| EP | 0853922 B1 | 2/2005 |
| EP | 1527747 A2 | 5/2005 |
| EP | 1530952 A1 | 5/2005 |
| EP | 1532932 A1 | 5/2005 |
| EP | 1535581 A2 | 6/2005 |
| EP | 1545360 A1 | 6/2005 |
| EP | 1609430 A1 | 12/2005 |
| EP | 1201192 | 2/2006 |
| EP | 1034746 B1 | 3/2006 |
| EP | 1632192 A1 | 3/2006 |
| EP | 1642543 A1 | 4/2006 |
| EP | 1645238 | 4/2006 |
| EP | 1645240 A2 | 4/2006 |
| EP | 1649821 A1 | 4/2006 |
| EP | 0875209 B1 | 5/2006 |
| EP | 1683496 A2 | 7/2006 |
| EP | 1685806 A2 | 8/2006 |
| EP | 1707143 | 10/2006 |
| EP | 1707151 A2 | 10/2006 |
| EP | 1545360 | 3/2007 |
| EP | 1767163 | 3/2007 |
| EP | 1767164 | 3/2007 |
| EP | 1769765 | 4/2007 |
| EP | 1769766 A1 | 4/2007 |
| EP | 1772109 | 4/2007 |
| EP | 1785097 | 5/2007 |
| EP | 1785098 | 5/2007 |
| EP | 1785101 | 5/2007 |
| EP | 1787597 | 5/2007 |
| EP | 1810625 | 7/2007 |
| EP | 1810628 A1 | 7/2007 |
| EP | 1842500 | 10/2007 |
| EP | 1852079 A1 | 11/2007 |
| EP | 1878400 | 1/2008 |
| EP | 1894535 | 3/2008 |
| EP | 1902681 A1 | 3/2008 |
| EP | 1902684 A1 | 3/2008 |
| EP | 1915957 A2 | 4/2008 |
| EP | 1915966 A1 | 4/2008 |
| EP | 1929970 A1 | 6/2008 |
| EP | 1946715 | 7/2008 |
| EP | 1958583 | 8/2008 |
| EP | 1990019 | 11/2008 |
| EP | 1994904 | 11/2008 |
| EP | 1997438 | 12/2008 |
| EP | 1997439 | 12/2008 |
| EP | 1527744 | 2/2009 |
| EP | 2044890 A1 | 4/2009 |
| EP | 2090245 A1 | 8/2009 |
| EP | 2092905 A1 | 8/2009 |
| EP | 2103268 | 9/2009 |
| EP | 2105104 | 9/2009 |
| EP | 2147649 | 1/2010 |
| EP | 2153791 | 2/2010 |
| EP | 2158523 A1 | 3/2010 |

(56) References Cited

FOREIGN PATENT DOCUMENTS

| | | |
|---|---|---|
| EP | 2206474 | 7/2010 |
| EP | 2209413 A1 | 7/2010 |
| EP | 1920725 | 10/2010 |
| EP | 2243439 | 10/2010 |
| EP | 2294998 | 3/2011 |
| EP | 2301467 | 3/2011 |
| EP | 2301468 A1 | 3/2011 |
| EP | 1628586 | 7/2011 |
| EP | 2344249 A1 | 7/2011 |
| EP | 2364660 A1 | 9/2011 |
| EP | 2392282 A1 | 12/2011 |
| EP | 2457532 A1 | 5/2012 |
| EP | 2529687 A2 | 12/2012 |
| GB | 0149058 A | 8/1920 |
| GB | 623316 A | 5/1949 |
| GB | 1490585 A | 11/1977 |
| GB | 2213416 A | 8/1989 |
| GB | 2214430 A | 9/1989 |
| JP | 61501068 | 9/1984 |
| JP | 2113454 | 9/1990 |
| JP | 6502328 | 3/1992 |
| JP | 55106 | 1/1993 |
| JP | H0540112 A | 2/1993 |
| JP | 6121797 A | 5/1994 |
| JP | 6285078 A | 10/1994 |
| JP | 6511401 | 12/1994 |
| JP | H06343644 A | 12/1994 |
| JP | 744792 | 2/1995 |
| JP | H07265328 A | 10/1995 |
| JP | 08056955 | 3/1996 |
| JP | 08252263 A | 10/1996 |
| JP | 8289895 | 11/1996 |
| JP | 8317934 | 12/1996 |
| JP | 8317936 | 12/1996 |
| JP | 09000538 A | 1/1997 |
| JP | H0910223 A | 1/1997 |
| JP | 9122138 A | 5/1997 |
| JP | 0010000195 A | 1/1998 |
| JP | H1024051 A | 1/1998 |
| JP | 10155798 | 6/1998 |
| JP | 1147149 | 2/1999 |
| JP | 1147150 | 2/1999 |
| JP | 11070124 | 3/1999 |
| JP | 11169381 | 6/1999 |
| JP | 11192238 | 7/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 | 1/2001 |
| JP | 2001029355 | 2/2001 |
| JP | 2001029356 | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2006015078 A | 1/2006 |
| JP | 2006501939 A | 1/2006 |
| JP | 2006095316 A | 4/2006 |
| JP | 2011125195 A | 6/2011 |
| JP | 2013128768 A | 7/2013 |
| JP | 0006030945 B2 | 11/2016 |
| SU | 401367 A1 | 10/1973 |
| WO | 8900757 | 1/1989 |
| WO | 9204873 | 4/1992 |
| WO | 9206642 | 4/1992 |
| WO | 9319681 | 10/1993 |
| WO | 9321845 | 11/1993 |
| WO | 9400059 | 1/1994 |
| WO | 9408524 | 4/1994 |
| WO | 9408638 A2 | 4/1994 |
| WO | 9420025 | 9/1994 |
| WO | 9502369 | 1/1995 |
| WO | 9507662 | 3/1995 |
| WO | 9515124 | 6/1995 |
| WO | 9520360 | 8/1995 |
| WO | 9520921 | 8/1995 |
| WO | 9605776 | 2/1996 |
| WO | 9611635 | 4/1996 |
| WO | 9611635 A1 | 4/1996 |
| WO | 9622056 | 7/1996 |
| WO | 9622056 A1 | 7/1996 |
| WO | 9613218 | 9/1996 |
| WO | 9700646 | 1/1997 |
| WO | 9700647 | 1/1997 |
| WO | 9710764 | 3/1997 |
| WO | 9718768 | 5/1997 |
| WO | 9724073 | 7/1997 |
| WO | 9724993 | 7/1997 |
| WO | 9814124 | 4/1998 |
| WO | 9827880 | 7/1998 |
| WO | 9831290 | 7/1998 |
| WO | 9843264 | 10/1998 |
| WO | 9857603 A1 | 12/1998 |
| WO | 9903407 | 1/1999 |
| WO | 9903408 | 1/1999 |
| WO | 9903409 | 1/1999 |
| WO | 9903414 | 1/1999 |
| WO | 9912488 | 3/1999 |
| WO | 9923933 | 5/1999 |
| WO | 9923933 A2 | 5/1999 |
| WO | 9923959 | 5/1999 |
| WO | 9925261 | 5/1999 |
| WO | 9925261 A1 | 5/1999 |
| WO | 9940857 | 8/1999 |
| WO | 9940861 A1 | 8/1999 |
| WO | 9951158 | 10/1999 |
| WO | 9966850 | 12/1999 |
| WO | 0024322 | 5/2000 |
| WO | 0024330 | 5/2000 |
| WO | 0024331 | 5/2000 |
| WO | 0033753 | 6/2000 |
| WO | 0036986 A1 | 6/2000 |
| WO | 0041638 | 7/2000 |
| WO | 0047124 | 8/2000 |
| WO | 0053112 | 9/2000 |
| WO | 0059392 A1 | 10/2000 |
| WO | 0066014 A1 | 11/2000 |
| WO | 0100114 A1 | 1/2001 |
| WO | 0101847 | 1/2001 |
| WO | 0115614 A1 | 3/2001 |
| WO | 0117448 | 3/2001 |
| WO | 0154604 A1 | 8/2001 |
| WO | 0166025 | 9/2001 |
| WO | 2001-082807 A1 | 11/2001 |
| WO | 02/07627 | 1/2002 |
| WO | 0234147 A1 | 5/2002 |
| WO | 0245589 A2 | 6/2002 |
| WO | 02058544 | 8/2002 |
| WO | 02067798 | 9/2002 |
| WO | 02080783 | 10/2002 |
| WO | 02080784 | 10/2002 |
| WO | 02080785 | 10/2002 |
| WO | 02080786 | 10/2002 |
| WO | 02080793 A1 | 10/2002 |
| WO | 02080794 | 10/2002 |
| WO | 02080795 | 10/2002 |
| WO | 02080796 | 10/2002 |
| WO | 02080797 | 10/2002 |
| WO | 02080798 | 10/2002 |
| WO | 02080799 | 10/2002 |
| WO | 02081170 | 10/2002 |
| WO | 02085218 | 10/2002 |
| WO | 02094746 | 11/2002 |
| WO | 03061500 | 7/2003 |

(56) References Cited

FOREIGN PATENT DOCUMENTS

| | | |
|---|---|---|
| WO | 03068046 | 8/2003 |
| WO | 03096880 | 11/2003 |
| WO | 03101311 | 12/2003 |
| WO | 03090630 A3 | 4/2004 |
| WO | 2004028585 | 4/2004 |
| WO | 2004028585 A2 | 4/2004 |
| WO | 2004032776 | 4/2004 |
| WO | 2004032777 | 4/2004 |
| WO | 2004052221 | 6/2004 |
| WO | 2004073488 | 9/2004 |
| WO | 2004073490 | 9/2004 |
| WO | 2004073753 | 9/2004 |
| WO | 2004082495 | 9/2004 |
| WO | 2004083797 | 9/2004 |
| WO | 2004098383 | 11/2004 |
| WO | 2004103156 | 12/2004 |
| WO | 05/004734 | 1/2005 |
| WO | 2005004735 | 1/2005 |
| WO | 2005009255 | 2/2005 |
| WO | 2005009255 A1 | 2/2005 |
| WO | 2005011049 | 2/2005 |
| WO | 2005011049 A2 | 2/2005 |
| WO | 2005030071 | 4/2005 |
| WO | 2005030071 A1 | 4/2005 |
| WO | 2005048809 | 6/2005 |
| WO | 2005048809 A1 | 6/2005 |
| WO | 2005050151 | 6/2005 |
| WO | 2005050151 A1 | 6/2005 |
| WO | 2005074364 A2 | 8/2005 |
| WO | 2005110263 A2 | 11/2005 |
| WO | 2006021269 A1 | 3/2006 |
| WO | 2005110264 A2 | 4/2006 |
| WO | 2006134483 A2 | 12/2006 |
| WO | 2008008457 | 1/2008 |
| WO | 2008008457 A2 | 1/2008 |
| WO | 2008040483 A1 | 4/2008 |
| WO | 2008042423 A2 | 4/2008 |
| WO | 2008045348 | 4/2008 |
| WO | 2008045350 | 4/2008 |
| WO | 2008102154 A2 | 8/2008 |
| WO | 2008-112147 A1 | 9/2008 |
| WO | 2008112147 | 9/2008 |
| WO | 2009-005850 A1 | 1/2009 |
| WO | 2009005850 | 1/2009 |
| WO | 2009032623 | 3/2009 |
| WO | 2009032623 A2 | 3/2009 |
| WO | 2009039179 | 3/2009 |
| WO | 2009039179 A1 | 3/2009 |
| WO | 2009039510 | 3/2009 |
| WO | 2009039510 A1 | 3/2009 |
| WO | 2009064346 A1 | 5/2009 |
| WO | 2009124097 | 10/2009 |
| WO | 2009124097 A1 | 10/2009 |
| WO | 2010033630 A1 | 3/2010 |
| WO | 2010104753 | 9/2010 |
| WO | 2011018154 A1 | 2/2011 |
| WO | 2011068795 A1 | 6/2011 |
| WO | 2012076844 A1 | 6/2012 |
| WO | 2012166845 A1 | 12/2012 |
| WO | WO-2012166845 A1 * 12/2012 ........... A61B 5/0205 |  |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Tinkcler L. F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Results with an Electrothermal Bipolar Vessel Sealer" Surgical Endoscopy (2000) 15:799-801. (4 pages).

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001. (1 page).

Bergdahl et al. "Studies on Coagulation and the Development of an Automatic Computerized Bipolar Coagulator" J. Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

(56) References Cited

OTHER PUBLICATIONS

Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surger" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
European Search Report dated Feb. 9, 2016, issued in European Application No. 15166527.
Japanese Office Action dated Feb. 4, 2019 issued in corresponding JP Appln. No. 2015-091734.

* cited by examiner

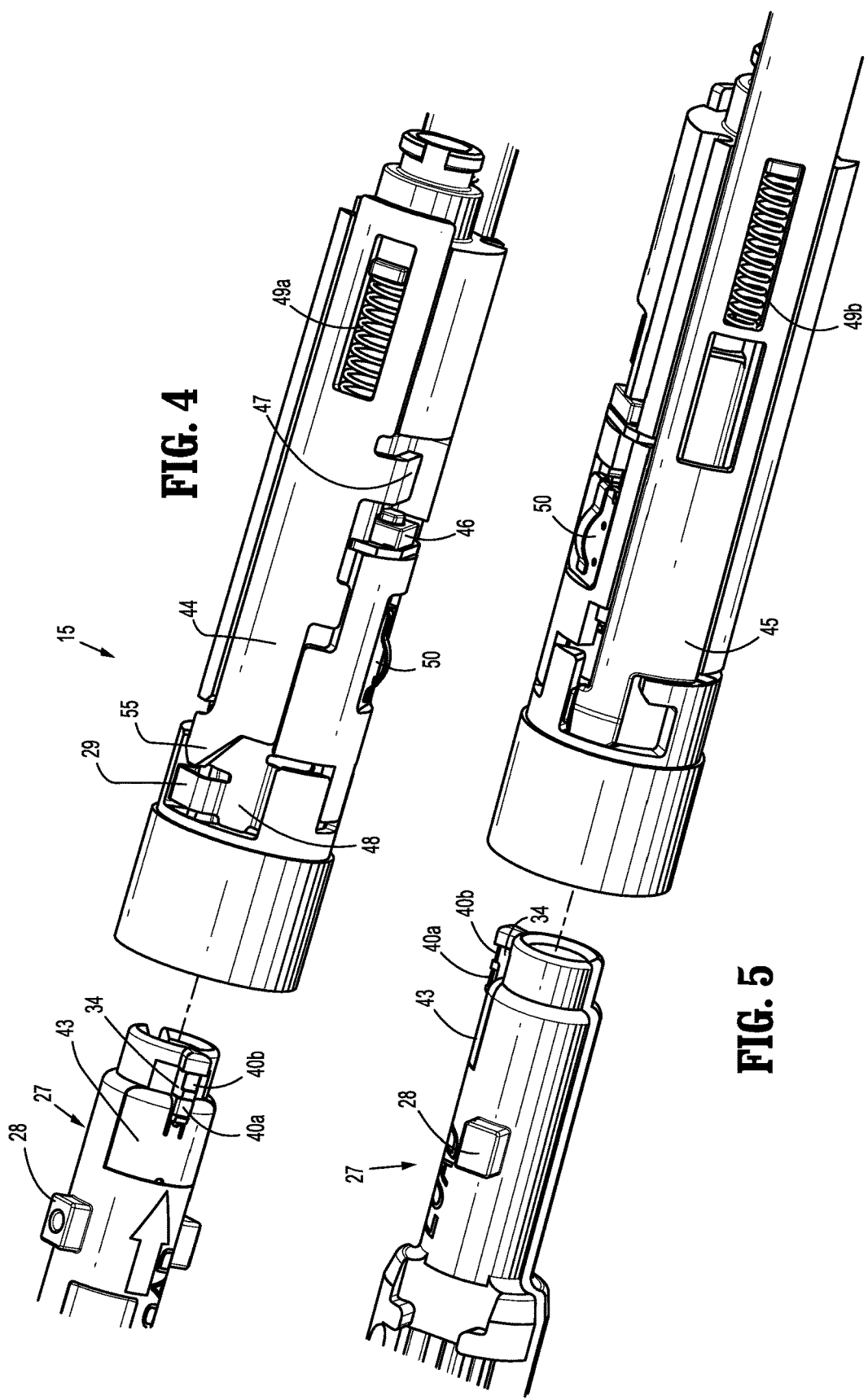

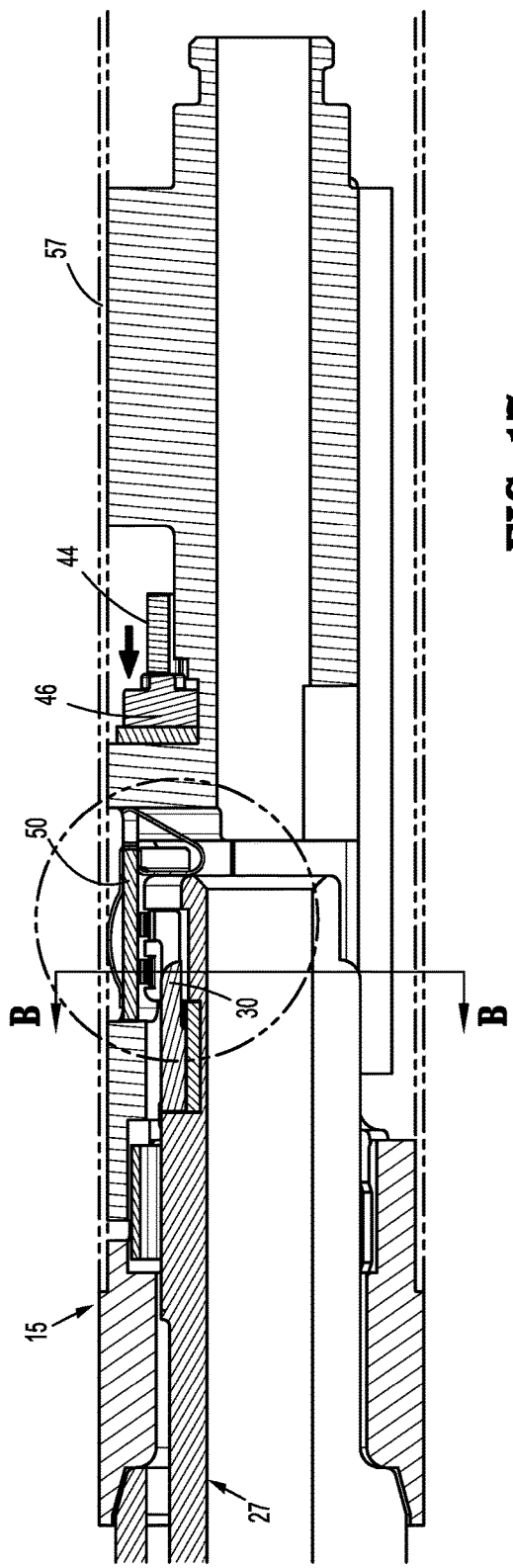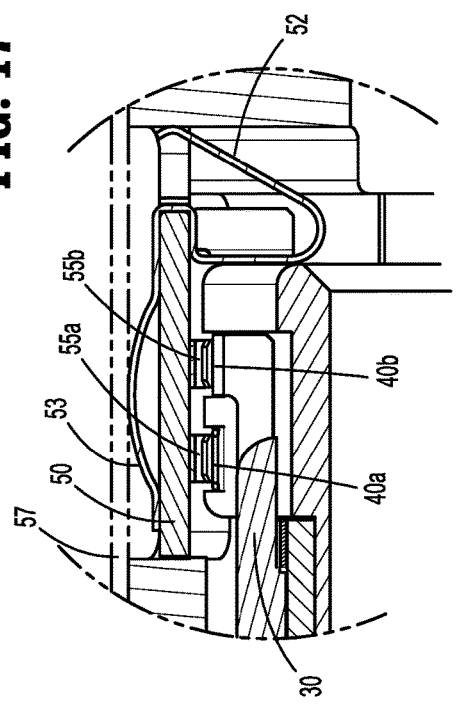

"A-A"

"B-B"

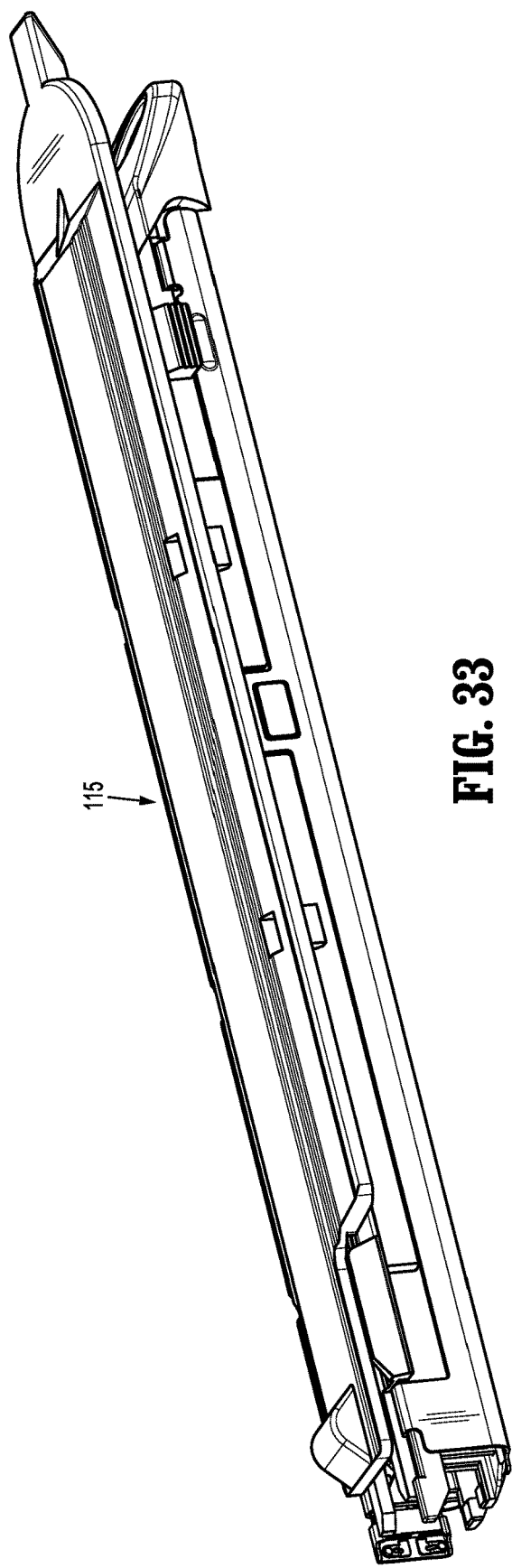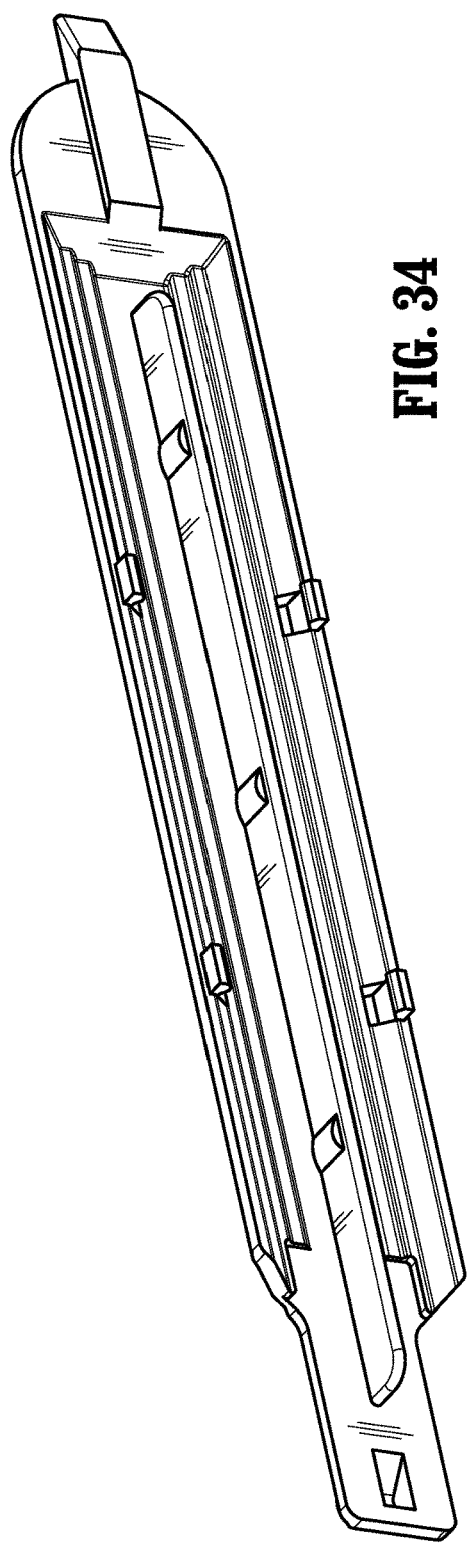

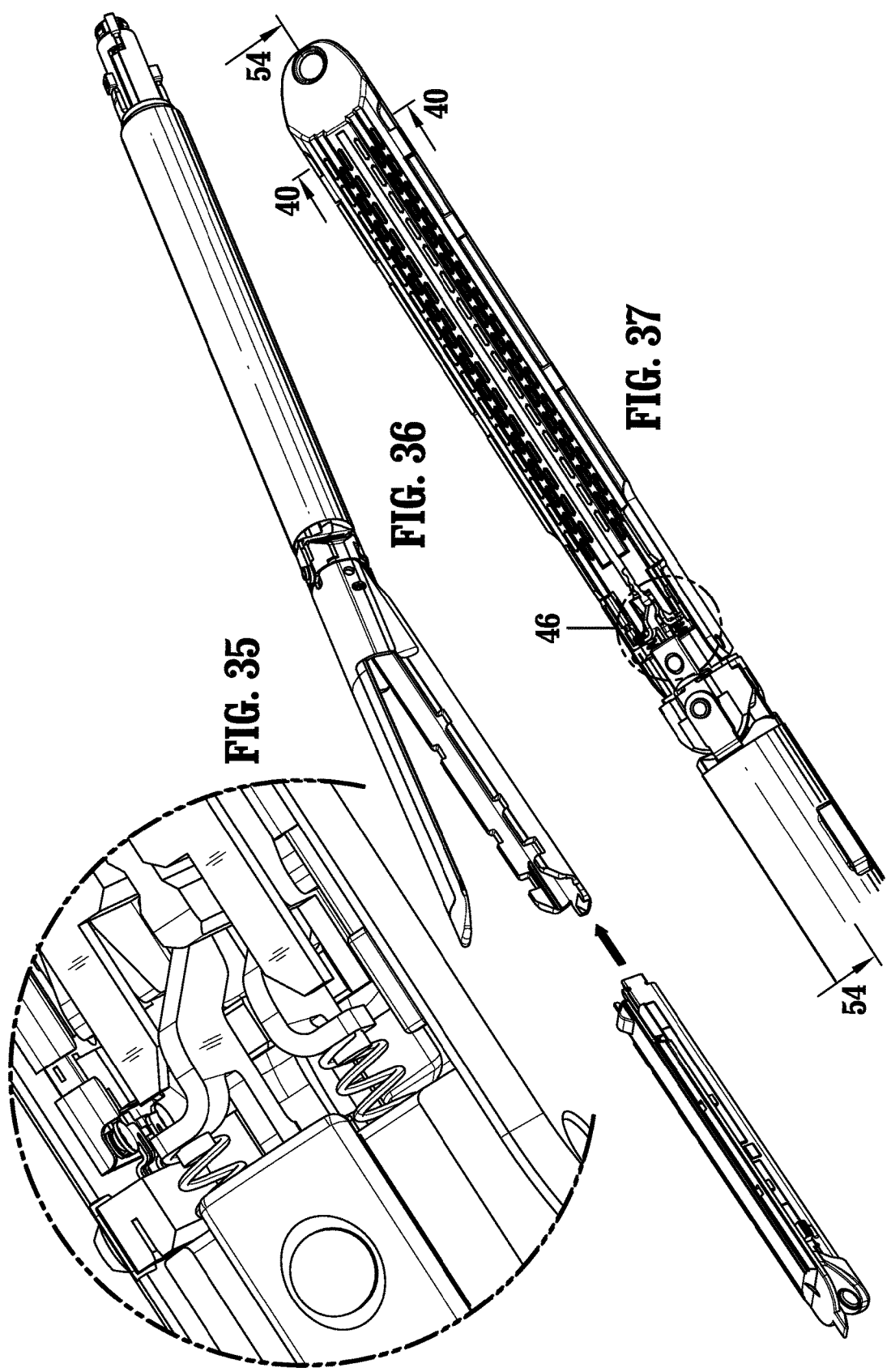

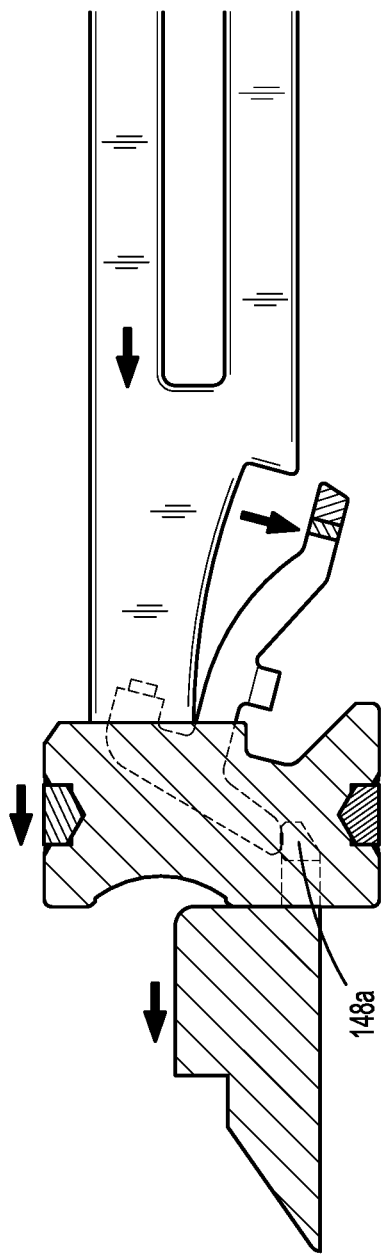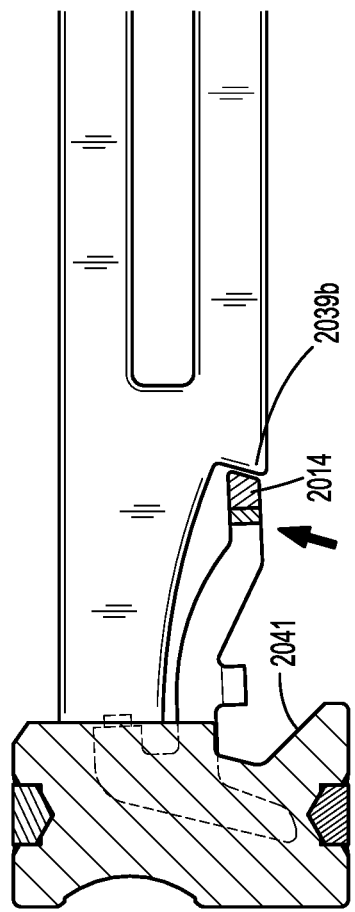
FIG. 56
FIG. 57

AUTHENTICATION AND INFORMATION SYSTEM FOR REUSABLE SURGICAL INSTRUMENTS

CROSS-REFERENCE TO RELATED APPLICATIONS

This application is a continuation of U.S. patent application Ser. No. 14/670,837, filed Mar. 27, 2015, which claims the benefit of and priority to U.S. Provisional Patent Application Ser. No. 61/989,609, filed May 7, 2014. The contents of each of the above applications are hereby incorporated by reference.

BACKGROUND

Technical Field

The present disclosure relates to surgical instruments having a reusable handle and removable and replaceable components, such as a disposable or replaceable loading unit. The present disclosure relates to printed circuit boards suitable for use in surgical devices. More particularly, the present disclosure relates to a communication protocol for a system in which data is communicated through a bus, the protocol eliminating the need for multiple buses for transmitting information from various components in the system.

Description of Related Art

Powered surgical instruments for use in endoscopic procedures are known. Typically, such instruments include a reusable handle assembly, and a replaceable and generally disposable component sometimes referred to as single use loading unit or SULU. An adapter assembly connects the loading unit, which can include an end effector for interacting with tissue, to the handle assembly. In the case of a surgical stapler, the end effector/tool assembly can include a replaceable cartridge that is changed after each firing of the surgical stapler. To reduce costs and shorten procedure times, the handle assemblies are generally configured for use with a variety of loading units and/or assemblies of various configurations for use on tissue having different properties, e.g., thickness and density. For example, the different loading units may have staples of different sizes and/or the staples may be arranged in different configurations. To ensure the handle assembly is programmed to operate with the attached loading unit, some loading units are provided with an integrated circuit, also known as a chip, that communicates with the handle assembly to identify the configuration of the loading unit.

Printed circuit boards (PCBs), sometimes referred to as printed wiring boards (PWBs) or etched wiring boards, are widely used in the assembly of discrete electrical components into operating circuits. PCBs generally provide a reliable and economical means of interconnecting electrical signals among system components. PCBs are available in a variety of different types and may be classified in a variety of ways.

PCBs are generally used to mechanically support and electrically connect electronic components using electrically-conductive pathways or signal traces that conduct signals on the PCB. A typical PCB includes one or more layers of insulating material upon which patterns of electrical conductors are formed. In addition to a pattern of conductive traces on the PCB, a patterned array of metal-filled through-holes, or vias, may be formed to allow for layer-to-layer interconnections among various conductive features.

PCBs may be classified as single-sided PCBs, double-sided PCBs, and multi-layer PCBs, according to the number of circuit pattern surfaces. PCBs may have circuits that perform a single function or multiple functions.

A typical PCB may include a variety of electronic components. Electronic components form parts of electronic circuitry and may be classified in a variety of ways. An electronic component may be classified as active or passive. In general, an active component is any type of circuit component with the ability to electrically control the flow of electrons or other electrically-charged particles. Some examples of active components are transistors, integrated circuits (ICs), and silicon-controlled rectifiers (SCRs). Components incapable of controlling current by means of another electrical signal are generally classified as passive components. Examples of passive components include capacitors, resistors, inductors, transformers, and diodes. A PCB on which electrical components are mounted is sometimes referred to as a printed circuit assembly (PCA) or a printed circuit board assembly (PCBA).

Electrical signals may be used on PCBs for controlling the operation of a surgical device. For example, electrical signals may be used on PCBs for controlling the delivery of surgical staples to tissue, and may be used for indicatory devices, e.g., to provide feedback to the surgeon relating to various tissue parameters or conditions. Some surgical systems include a powered hand-held surgical device, a surgical loading unit (sometimes referred to as a disposable loading unit or a disposable end effector), and an adapter for selectively interconnecting the surgical loading unit and the surgical device. Certain types of adapters enable the surgical device to drive a multitude of functions of surgical loading units of various configurations.

In order for the surgical device to drive the various functions of the surgical loading unit or assembly so that the surgical system performs properly, a controller may be associated with the surgical device and configured to receive various information, such as information about the type of adapter and/or the type of loading unit. For example, the different surgical loading units may have staples of different sizes and/or the staples may be arranged in different configurations. To ensure the surgical device is programmed to operate with the attached surgical loading unit, some reload assemblies are provided with an integrated circuit, also known as a chip, which communicates with the surgical device to identify the configuration of the surgical loading unit.

To ensure the reliability of the surgical system, it is desirable to confirm whether the surgical loading unit and the adapter have been previously used, and, if so, to count how many times the surgical reload assembly has been used. Data communications between the surgical loading unit and the surgical device may pass through a physical connection of an interface between the adapter and the surgical device.

It would be desirable to develop a communication protocol for use in a surgical system for efficiently and effectively transmitting information from various components in the system.

SUMMARY

In an aspect of the present disclosure, a method of communicating data through a bus comprises providing a microprocessor capable of demultiplexing transmit and receive lines, providing a first microchip and a second microchip in a surgical system, each of the first and second microchips configured to provide authentication of a first component and a second component in the surgical system, each of the first and second microchips being communicatively-coupled through a bus to the microprocessor; and controlling a receive mode and a transmit mode over the bus.

The method can further comprise receiving at least one signal from the first microchip or the second microchip using the receive mode over the bus. Receiving at least one signal can include selecting the receive mode utilizing the microprocessor. The method can further comprise transmitting at least one signal to the first microchip or the second microchip using the transmit mode over the bus. Transmitting at least one signal can include selecting the transmit mode utilizing the microprocessor.

The method can further comprise providing a third microchip connected to the microprocessor, the third microchip having a data wire and a ground wire.

The method can further comprise receiving at least one signal from the first microchip or the second microchip, including turning on the ground wire of the first microchip or second microchip. The method can further comprise transmitting at least one signal from the first microchip or the second microchip, including turning off the ground wire of the first microchip or second microchip.

In another aspect, a method of communicating data through a bus comprises authenticating a surgical component utilizing a microchip communicatively-coupled through a bus to a microprocessor capable of demultiplexing transmit and receive lines, and controlling a receive mode and a transmit mode over the bus.

Authenticating can include utilizing the microchip. Authenticating can further include utilizing a one-wire data interface of the microchip.

The method can further comprise receiving at least one signal from the surgical component using the receive mode over the bus. Receiving at least one signal from the surgical component using the receive mode over the bus can include turning on the ground wire of the microchip. The microprocessor can be used to select the receive mode.

The method can further comprise transmitting at least one signal to the microprocessor using the transmit mode over the bus. Transmitting at least one signal to the microprocessor using the transmit mode over the bus can include turning off the ground wire of the microchip. Transmitting at least one signal to the microprocessor using the transmit mode over the bus can further include utilizing the microprocessor to select the transmit mode.

In certain embodiments, the surgical component has a second microchip. The microprocessor can be part of a controller for a surgical system, the surgical component being a part of the surgical system.

In another aspect, a surgical system, comprises a handle assembly having a controller, the controller having at least one program, an adapter assembly, and a loading unit having a tool assembly and at least one chip assembly having a chip storing data indicating whether the tool assembly articulates or not, the controller including a microprocessor configured for de-multiplexing data from said chip.

The controller can read the data and not drive an articulation link in the adapter assembly and/or loading unit if the data indicated that the loading unit does not articulate.

In yet another aspect, a surgical system, comprises a handle assembly having a controller, the controller having at least one program, an adapter assembly, and a loading unit having a tool assembly and at least one chip assembly having a chip storing data indicating the maximum drive force for the loading unit, the controller including a microprocessor configured for de-multiplexing data from said chip.

The controller can be is programmed to read the data, and also read a drive force from a sensor, wherein the controller does not drive a member in the adapter assembly and/or loading unit if the drive force indicates that the maximum drive force has been reached.

The controller can be programmed to read the data, and also read a drive force from a sensor, wherein the controller operates in slow mode if the drive force indicates that the maximum drive force has been reached.

The chip can also store information about the type of loading unit. The loading unit can include a removable and replaceable staple cartridge assembly. The removable and replaceable staple cartridge assembly can include a chip storing data concerning the staple cartridge assembly

BRIEF DESCRIPTION OF THE DRAWINGS

The above and other aspects, features, and advantages of the present disclosure will become more apparent in light of the following detailed description when taken in conjunction with the accompanying drawings in which:

FIG. 4 is an enlarged view of the proximal end of the loading unit and the distal end of the adapter assembly shown in FIG. 3;

FIG. 5 is another enlarged view of the proximal end of the loading unit and the distal end of the adapter assembly shown in FIG. 3;

FIG. 17 is a cross-sectional, side view of the adapter assembly shown in FIG. 3 showing the adapter assembly engaged with the loading unit;

FIG. 18 is an enlarged view of the indicated area shown in FIG. 17 showing the adapter board engaged with the authentication board;

FIG. 33 is a top perspective view of the staple cartridge assembly of FIG. 32, with a shipping wedge;

FIG. 34 is a bottom perspective view of the shipping wedge of FIG. 33;

FIG. 35 is a detailed perspective view of a lockout assembly in accordance with embodiments of the present disclosure;

FIG. 36 is a perspective view of the loading unit of FIG. 23 showing the staple cartridge assembly;

FIG. 37 is a top view of the loading unit with the anvil and shipping wedge removed;

FIG. 56 is a side view of the drive beam, dynamic clamping member, and sled;

FIG. 57 is a side view of the drive beam, dynamic clamping member, and sled, with the drive beam and dynamic clamping member advanced.

DETAILED DESCRIPTION

Figure 1:
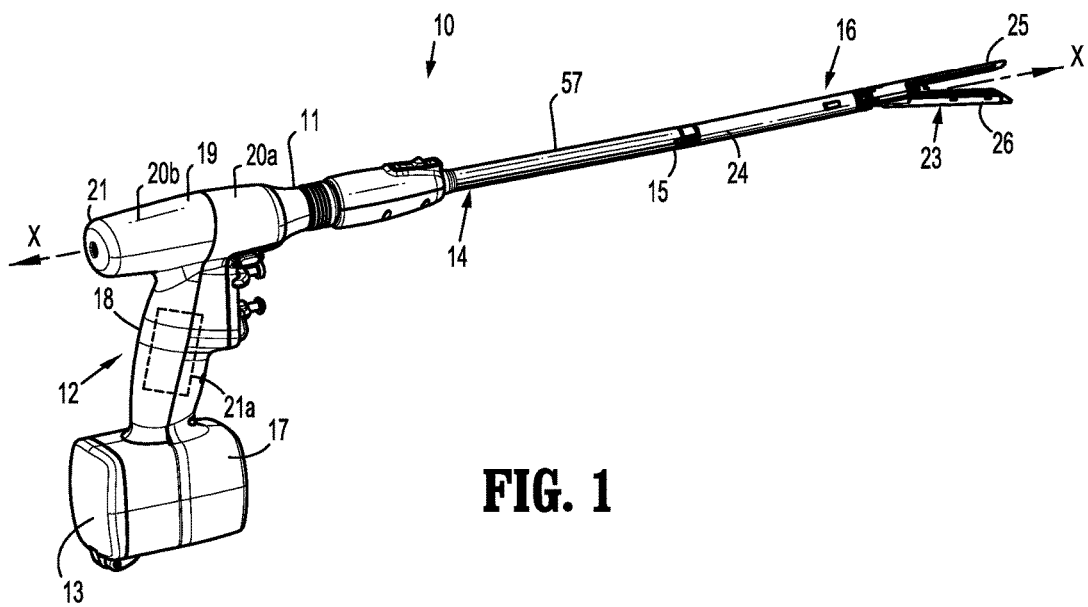
FIG. 1 is a perspective view of a surgical stapling device for use with a chip assembly according to embodiments of the present disclosure.

Particular embodiments of the present disclosure are described hereinbelow with reference to the accompanying drawings; however, it is to be understood that the disclosed embodiments are merely examples of the disclosure, which may be embodied in various forms. Well-known and/or repetitive functions and constructions are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. As is common in the art, the term "proximal" refers to that part or component closer to the user or operator, i.e. surgeon or clinician, while the term "distal" refers to that part or component further away from the user. In addition, as used herein in the description and in the claims, terms referencing orientation, e.g., "top", "bottom", "upper", "lower", "left", "right", and the like, are used with reference to the figures and features shown and described herein. It is to be understood that embodiments in accordance with the present disclosure may be practiced in any orientation without limitation. In this description, as well as in the drawings, like-referenced numbers represent elements which may perform the same, similar, or equivalent functions. Embodiments of the presently disclosed chip assembly will now be described in detail with reference to the drawings in which like reference numerals designate identical or corresponding elements in each of the several views. The word "exemplary" is used herein to mean "serving as an example, instance, or illustration." Any embodiment described herein as "exemplary" is not necessarily to be construed as preferred or advantageous over other embodiments. The word "example" may be used interchangeably with the term "exemplary."

This description may use the phrases "in an embodiment," "in embodiments," "in some embodiments," or "in other embodiments," which may each refer to one or more of the same or different embodiments in accordance with the present disclosure.

As it is used in this description, "printed circuit board" (or "PCB") or "circuit boards" generally refers systems that provide, among other things, mechanical support to electrical devices and/or components, electrical connection to and between these electrical components, combinations thereof, and the like. For the purposes herein, the term "printed circuit board" is interchangeable with the term "printed wiring board" and either is represented herein by the acronym PCB.

Figure 2:
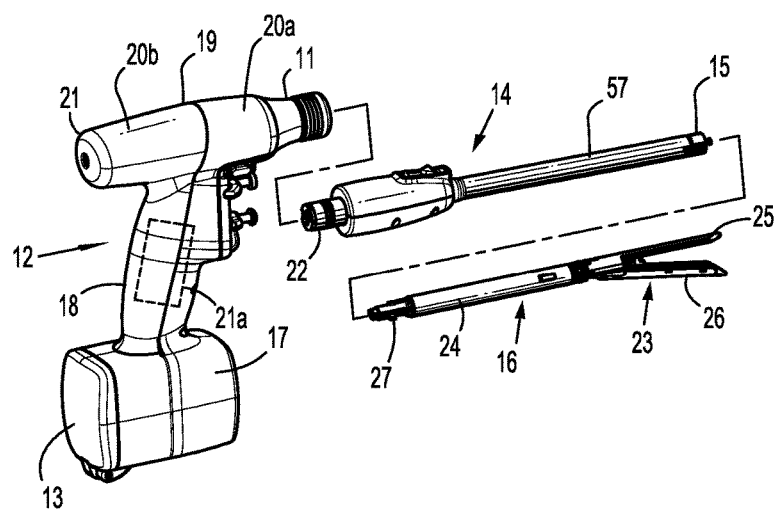
FIG. 2 is a perspective view of the surgical stapling device of FIG. 1 showing the handle assembly, adapter assembly, and loading unit in a separated configuration.

With reference initially to FIGS. 1 and 2, a surgical stapling instrument including an authentication system according to the present disclosure is shown generally as stapler 10. Stapler 10 includes a handle assembly 12, an adapter assembly 14 extending distally from handle assembly 12, and a loading unit 16 selectively secured to a distal end of adapter assembly 14. A detailed description of handle assembly 12, adapter assembly 14, and loading unit 16 is provided in commonly-owned U.S. Patent Appl. Publ. No. 2012/0089131, the contents of which is incorporated herein by reference in its entirety.

Handle assembly 12 includes a lower housing portion 17, an intermediate housing portion 18 extending from and/or supported on lower housing portion 17, and an upper housing portion 19 extending from and/or supported on intermediate housing portion 18. Intermediate housing portion 18 and upper housing portion 19 are separated into a distal half-section 20a that is integrally formed with, and extends from, the lower housing portion 17, and a proximal half-section 20b joined to distal half-section 20a by any suitable manner of attachment, such as without limitation, ultrasonic welding and/or a plurality of fasteners. When joined, distal and proximal half-sections 20a, 20b form a handle housing 21 defining a cavity therein which houses a circuit board that includes a controller 21a, and a drive mechanism (not shown).

Lower housing portion 17 includes a door 13 pivotally connected thereto for accessing a cavity formed in lower housing portion 17 for retaining a battery (not shown) therein. It is contemplated that stapler 10 may be powered by any number of power sources, such as, for example and without limitation, a fuel cell, a power cord connected to an external power source, and so forth.

Adapter assembly 14 includes a drive coupler 22 at a proximal end thereof and a loading unit coupler 15 at a distal end thereof. Distal half-section 20a of upper housing portion 19 defines a nose or connecting portion 11 configured to operably receive drive coupler 22 of adapter assembly 14. Loading unit 16 includes an adapter coupler 27 configured to operably receive loading unit coupler 15 of adapter assembly 14.

Upper housing portion 19 of handle housing 21 encloses a drive mechanism (not shown) configured to drive shafts and/or gear components (not shown) in order to perform the various operations of stapler 10. In particular, the drive mechanism is configured to drive shafts and/or gear components in order to selectively move a tool assembly or end effector 23 of loading unit 16 relative to a proximal body portion 24 of loading unit 16, to rotate loading unit 16 about a longitudinal axis "X-X" (FIG. 1) relative to handle housing 21, to move an anvil assembly 25 relative to cartridge assembly 26 of loading unit 16, and/or to fire a stapling and cutting cartridge within cartridge assembly 26 of loading unit 16.

The loading unit 16 shown in the FIGS. 1-21 is a linear surgical stapling loading unit. The loading unit includes a stapling anvil with recesses for forming surgical staples that are driven against it by operation of the loading unit in the surgical system. A staple cartridge houses the surgical staples, as well as the staple firing and/or driving assembly. The staple firing and/or driving assembly is known. One such assembly is described in U.S. Pat. Nos. 8,256,656 and 7,044,353, the entire disclosures of which are hereby incorporated by reference herein. The drive assembly includes an elongated drive beam having a knife blade. The drive beam pushes an actuation sled having wedge shaped surfaces for interacting with pushers. The pushers support the staples and have camming surfaces that the sled wedge shaped surfaces slide against, driving the pushers upwardly while the sled is advanced in a longitudinal fashion through the staple cartridge.

It is contemplated that the loading unit has jaw members for supporting the anvil and the staple cartridge respectively. The anvil jaw member and staple cartridge jaw member can be approximated to clamp tissue therebetween. It is also contemplated that the end effector can articulate or pivot off axis from the longitudinal axis defined by the proximal body portion 24.

It is contemplated that the loading unit can be a circular surgical stapling unit, other types of stapling units, or other types of surgical end effectors, such as electrocautery, ablation, ultrasonic, etc.

Figure 3:
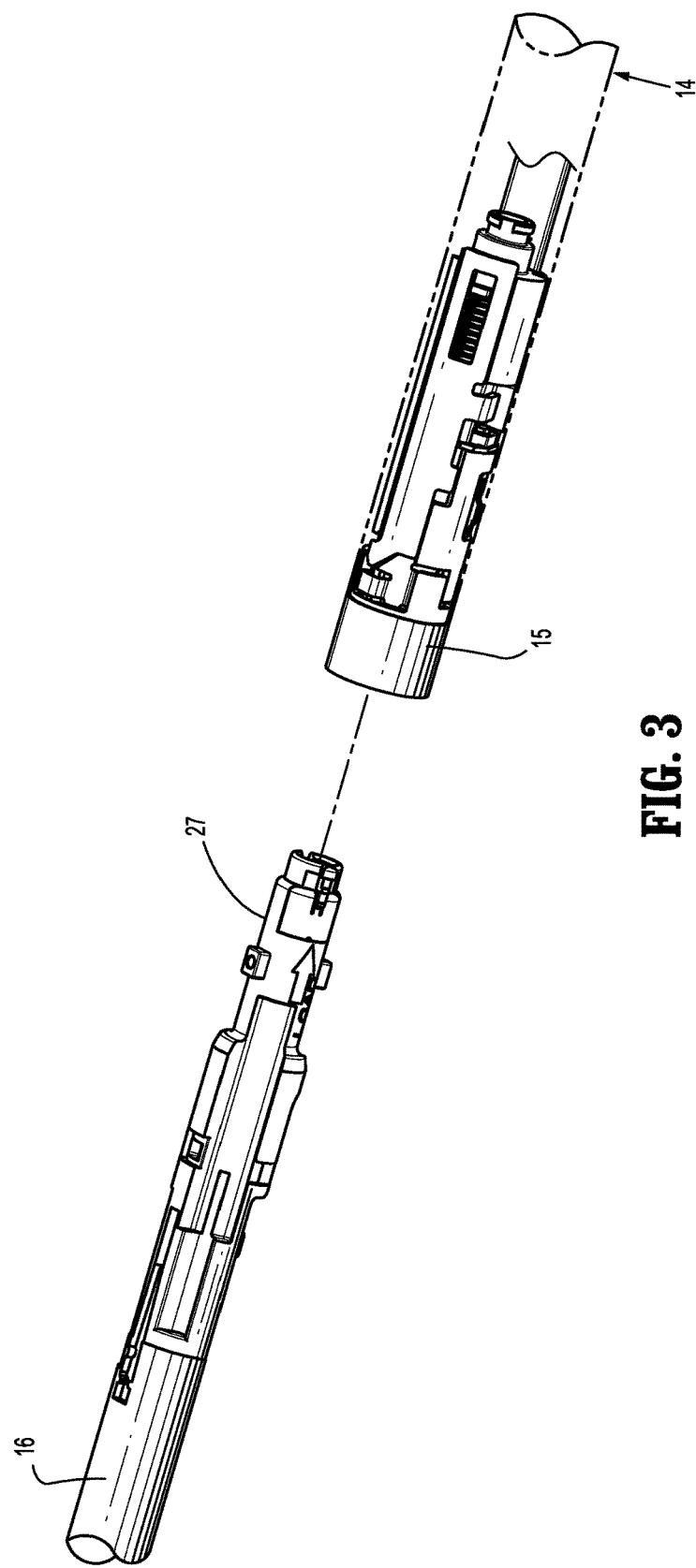
FIG. 3 is a view of a proximal end of a loading unit and a distal end of an adapter assembly of the surgical stapling device shown in FIG. 1.
Figure 6:
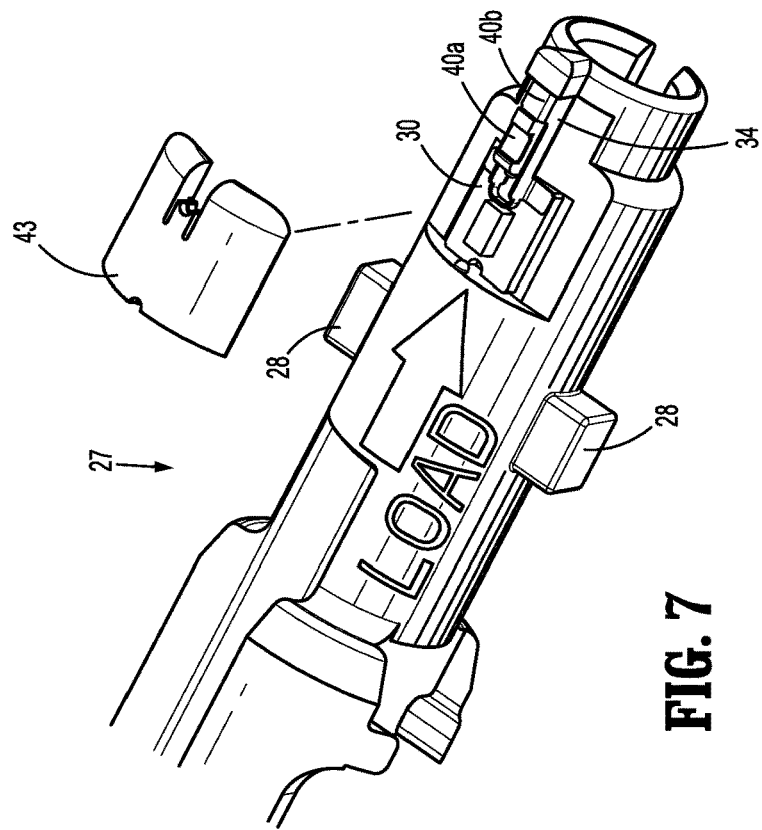
FIG. 6 is an enlarged, exploded view of the proximal end of the loading unit shown in FIG. 3 with the loading unit and authentication board separated.

With reference to FIGS. 3, 4, and 5, loading unit coupler 15 of adapter assembly 14 is configured to operably engage adapter coupler 27 of loading unit 16 via a push and twist or bayonet-type arrangement. Adapter coupler 27 includes one or more bayonet lugs 28 that are configured to mate with corresponding one or more bayonet channels 29 defined in a bayonet collar 48 provided by loading unit coupler 15 of adapter assembly 14. A short link member 44 and a load link member 45 are longitudinally disposed within adapter assembly 14 and are configured to translate longitudinally (e.g., distally and proximally) during operation of stapler 10. A cam 55 disposed at a distal end of short link member 44 is urged distally against a bayonet channel 29 by spring 49a. To engage loading unit 16 with adapter assembly 14, adapter coupler 27 of loading unit 16 is inserted into loading unit coupler 15 of adapter assembly 14 and rotated. In turn, bayonet collar 48 rotates cooperatively with adapter coupler 27. As bayonet collar 48 rotates, cam 55 rides off bayonet channel 29, causing short link member 44 to translate distally, which, in turn, causes a switch tab 47 formed in short link member 44 to actuate switch 46. Switch 46 is in operative electrical communication with the controller 21a and is configured to convey thereto the engagement status between loading unit 16 and adapter assembly 14.

Figure 11:
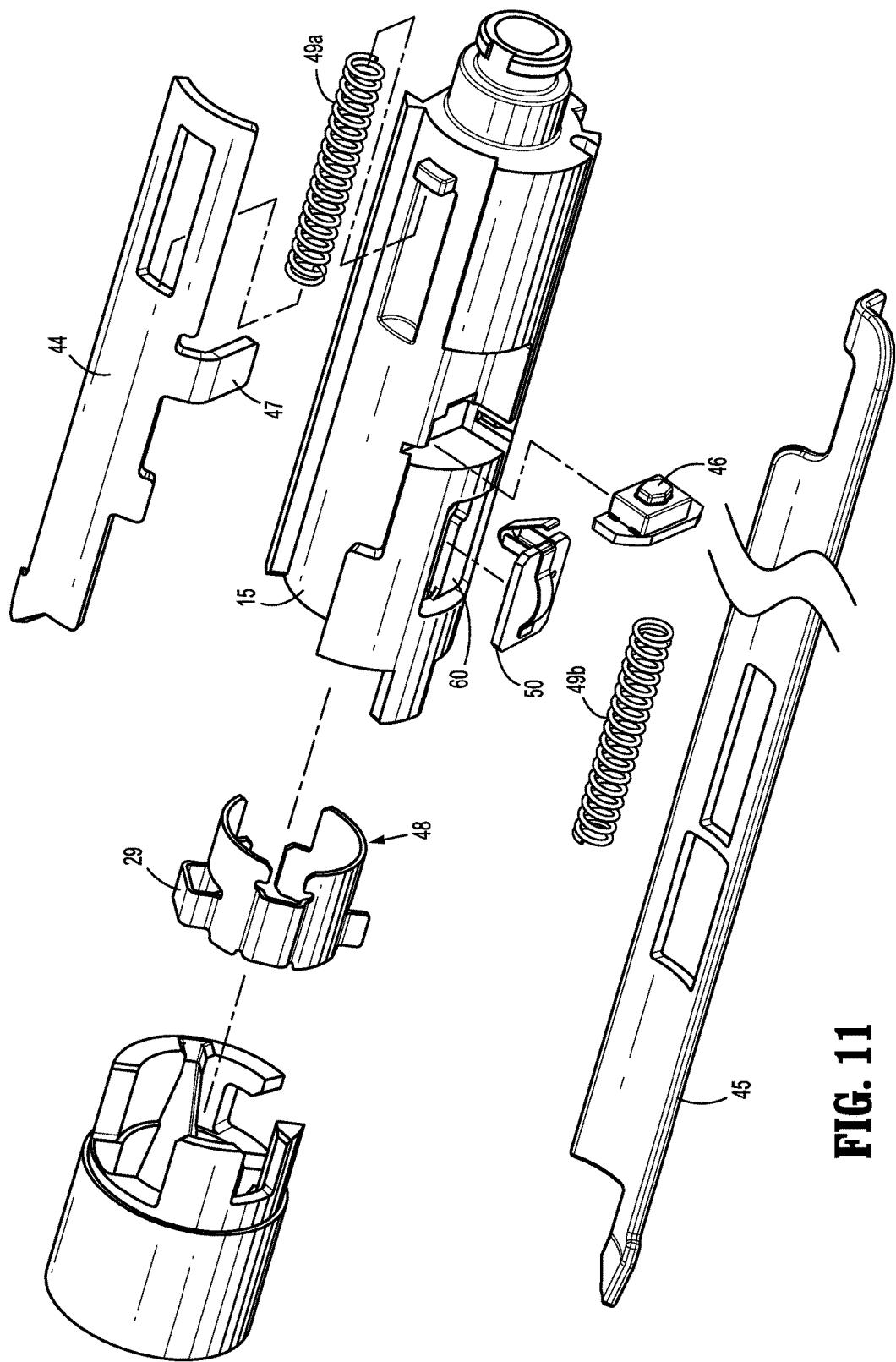
FIG. 11 is an enlarged, exploded view of the distal end of the adapter assembly shown in FIG. 3 with the adapter assembly and adapter board separated.
Figure 12:
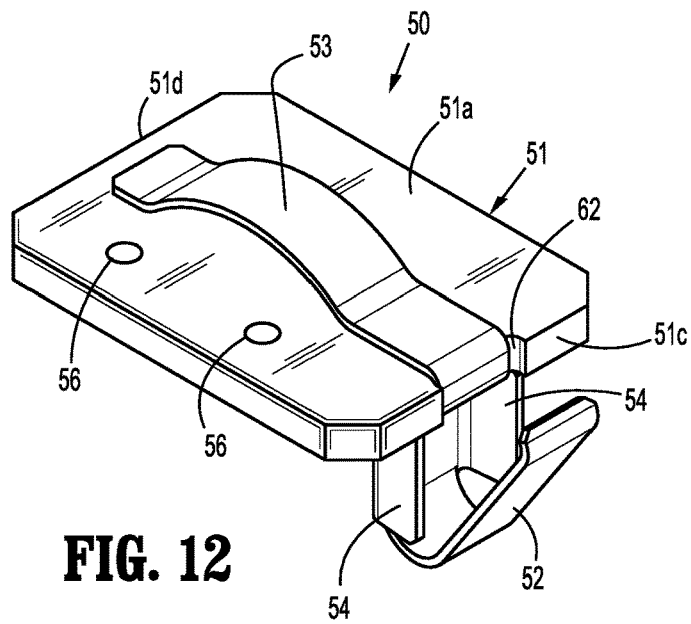
FIG. 12 is an enlarged view of the adapter board shown in FIG. 11.
Figure 13:
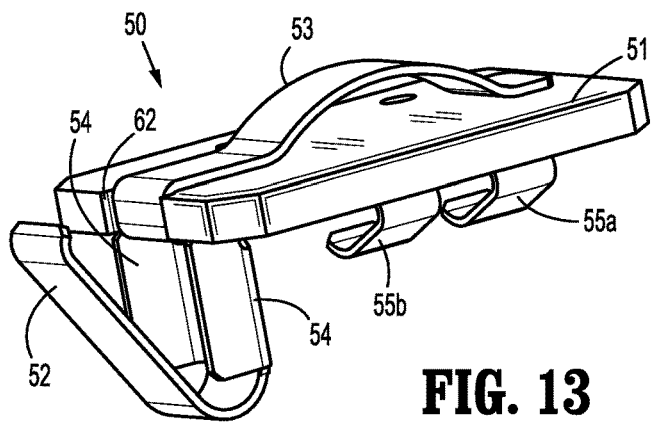
FIG. 13 is another enlarged view of the adapter board shown in FIG. 11.
Figure 14:
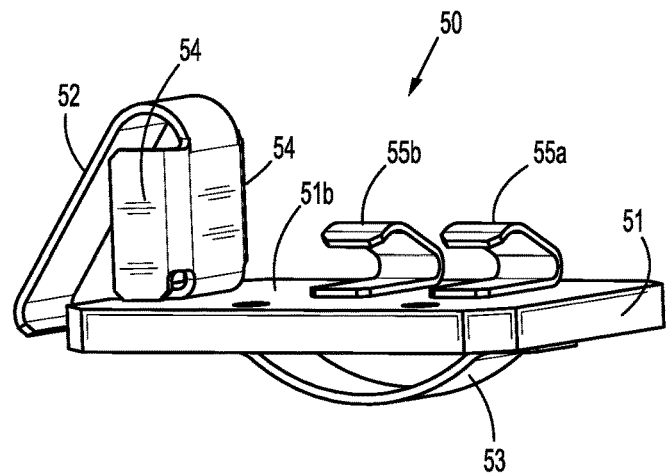
FIG. 14 is yet another enlarged view of the adapter board shown in FIG. 11.

Turning now to FIGS. 6-10, adapter coupler 27 of loading unit 16 includes an authentication board assembly 30 that is configured to be securely mounted within a recess 31 defined in adapter coupler 27. Authentication board assembly 30 is positioned within adapter coupler 27 such that when loading unit 16 is secured to adapter assembly 14, authentication board assembly 30 engages an adapter board assembly 50 mounted within loading unit coupler 15 of the adapter assembly (FIG. 11). In more detail, authentication board 30 includes a circuit board 37, a pair of contact members 40a, 40b (collectively, contact members 40) and a chip 36. Circuit board 37 defines a substantially planar elongated member configured to be securely received within recess 31 defined by adapter coupler 27. Chip 36 is in electrical communication with contact members 40. A distal end 37a of circuit board 37 supports chip 36, and a proximal end 37b of circuit board 37 supports contact members 40. Distal end 37a of circuit board 37 includes an alignment notch 33 defined therein that is configured to engage a corresponding alignment nub 32 provided at a distal end of recess 31 to ensure secure and accurate positioning of authentication board assembly 30 within adapter coupler 27.

Chip 36 includes any chip capable of storing the specifications of loading unit 16, such as, without limitation, cartridge size, staple arrangement, staple length, clamp-up distance, date of manufacture, expiration date, compatibility characteristics, a unique identifier (e.g., a serial number), and/or number of uses, and transmitting the specifications to handle assembly 12. In some embodiments, chip 36 includes an erasable programmable read only memory ("EPROM") chip. In this manner, the handle assembly 12 may adjust the firing forces, firing stroke, and/or other operational characteristics thereof in accordance with the specifications of loading unit 16 that are transmitted from chip 36. It is further envisioned that chip 36 may include write capabilities which allow handle assembly 12 to communicate to chip 36 that the associated loading unit 16 has been used, which can prevent reloading or reuse of an expended reload assembly, or any other unauthorized use.

In some embodiments, chip 36 includes a secure authentication chip, such as, without limitation, a DS28E15 Deep-Cover™ Secure Authenticator with 1-Wire SHA-256 and 512-Bit User EEPROM, manufactured by Maxim Integrated™ of San Jose, Calif. In these embodiments, the contents of chip 36, and the communications between chip 36 and handle assembly 12, are encrypted to prevent unauthorized access. In this manner, the use of low-quality counterfeit, re-manufactured, or "knock-off" loading units is effectively discouraged, which, in turn, reduces risk to patients by ensuring that only fresh, authentic loading units 16 are used during surgical procedures. In addition, the likelihood that medical facilities and/or surgeons may unwittingly use counterfeit loading units is greatly curtailed, thus reducing the overall costs to society for delivering medical services. In some embodiments, chip 36 utilizes a "1-wire" communications interface whereby a single signal conductor is employed, together with a ground conductor, for bidirectional serial communications between chip 36 and handle assembly 12.

Contact assembly 38 (FIGS. 9, 10) includes a short contact arm 41 and a long contact arm 42 joined by a contact base 59, and having a generally elongated u-shaped configuration. Short contact arm 41 includes a first contact member 40a orthogonally disposed and fixed to an upper portion of a proximal end thereof. Long contact arm 42 includes a second contact member 40b orthogonally disposed and fixed to an upper portion of a proximal end thereof. Short and long contact arms 41, 42 each include a solder tab 39 orthogonally disposed and fixed to a lower portion of a distal end thereof. Solder tabs 39 are electromechanically joined to a proximal end 37b of circuit board 37 by, e.g., soldering, electrically conductive adhesive, and/or other suitable technique.

Figure 7:
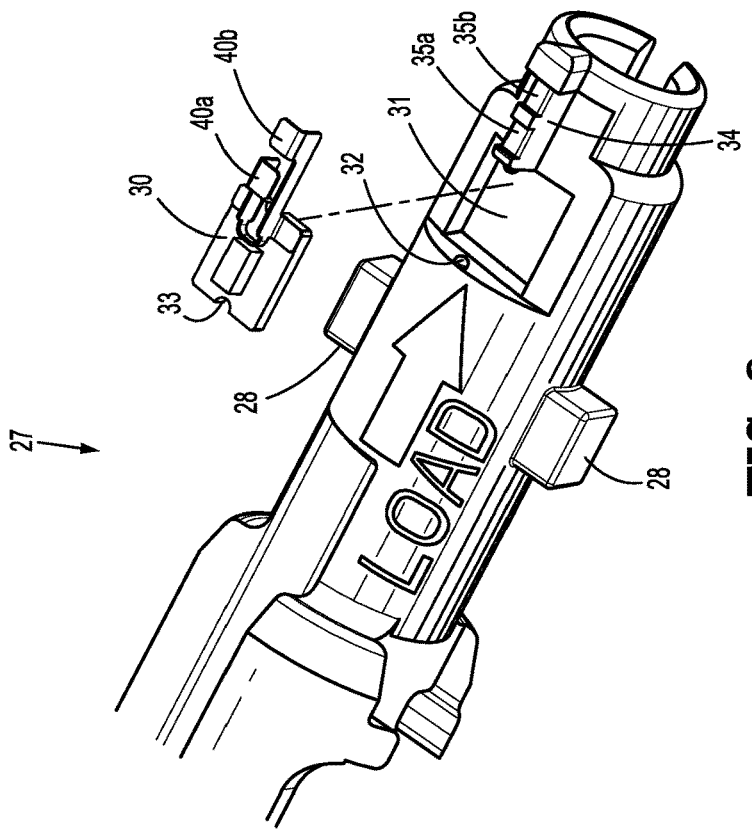
FIG. 7 is an enlarged, partially-exploded view of the proximal end of the loading unit shown in FIG. 3 with the authentication board cover separated from the loading unit.
Figure 8:
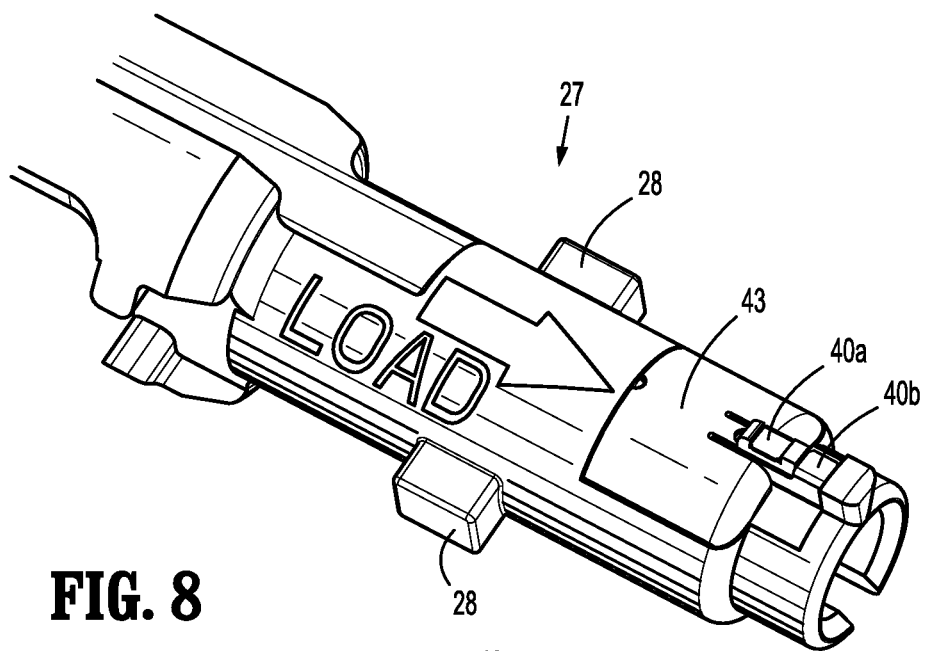
FIG. 8 is an enlarged view of the proximal end of the loading unit shown in FIG. 3.
Figure 9:
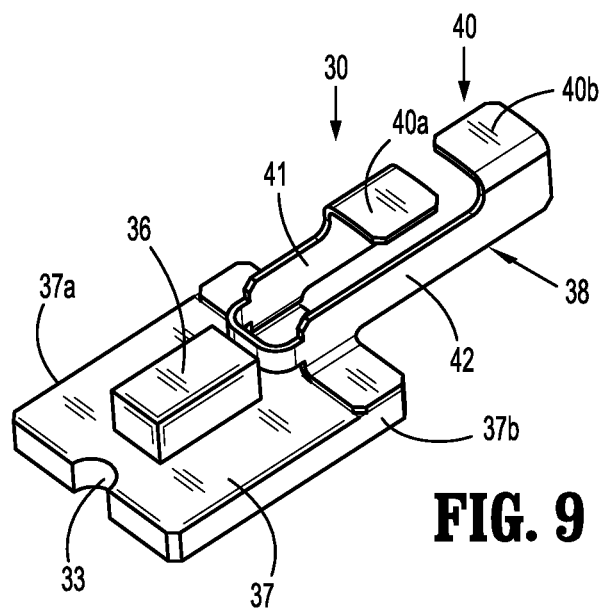
FIG. 9 is a perspective view of an authentication board assembly according to an embodiment of the present disclosure.
Figure 10:
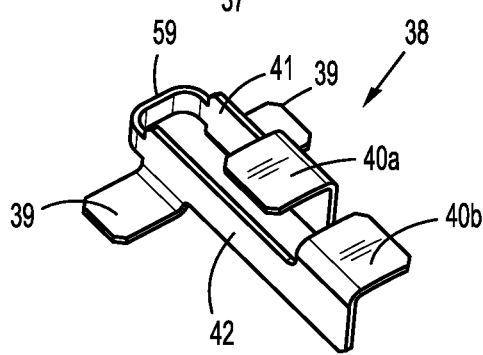
FIG. 10 is a perspective view of an authentication board contact.

Adapter coupler 27 includes a raised contact support 34 extending radially from a proximal end thereof and includes a pair of cradles 35a, 35b defined therein that are configured to receive first contact member 40a and second contact member 40b, respectively, when authentication board assembly 30 is positioned within recess 31 of adapter coupler 27. A cover 43 is configured to enclose and retain authentication board assembly 30 within recess 31 of adapter coupler 27 (FIGS. 7 and 8).

In some embodiments, short contact arm 41 and first contact member 40a are electrically insulated from long contact arm 42 and second contact member 40b by contact base 59. In these embodiments, each of short contact arm 41 and long contact arm 42 carries a separate circuit, e.g., short contact arm 41 carries signal and long contact arm 42 carries ground. In other embodiments, short contact arm 41 and first contact member 40a are electrically joined with long contact arm 42 and second contact member 40b. In these embodiments, short contact arm 41 and long contact arm 42 operate in a bifurcated or redundant mode to carry a signal circuit, while the ground circuit is carried through other electrically conductive components of loading unit 16, adapter unit 14, and/or handle assembly 12.

As mentioned above, authentication board assembly 30 is configured to engage adapter board assembly 50 mounted within loading unit coupler 15 when loading unit 16 is secured to adapter assembly 14. With reference now to FIGS. 11-14, loading unit coupler 15 includes an adapter board assembly 50 that is configured to be floatingly mounted within a pocket 60 defined in loading unit coupler 15. Adapter board assembly 50 is positioned within loading unit coupler 15 such that when loading unit 16 is secured to adapter assembly 14, adapter board assembly 50 engages authentication board assembly 30.

Adapter board assembly 50 includes a circuit board 51 having a pair of contact members 55a, 55b (collectively, contact members 55) fixed thereto and in operable communication with handle assembly 12. In the illustrated embodiment, contact members 55a, 55b are arranged for effective engagement in a transverse direction, e.g., transverse to the longitudinal axis "X-X" of stapler 10, to accommodate the rotational coupling of loading unit 16 and adapter assembly 14 as described herein.

Circuit board 51 includes an upper surface 51a, a lower surface 51b, a proximal end 51c, and a distal end 51d. Circuit board 51 defines a substantially planar elongated member configured to be resiliently or floatingly received within pocket 60 defined by loading unit coupler 15. A spring clip 52 is fixed to a proximal end 51c of circuit board 51 and is configured to support adapter board assembly 50 within pocket 60. Spring clip 52 includes a pair of spring supports 54 having a wing-like configuration that are configured prevent spring clip 52 from over-extension and to provide stiffness thereto. Adapter board assembly 50 includes a spring 53 having a broad, curvate u-shaped profile disposed on an upper surface 51a of circuit board 51. In some embodiments, spring clip 52 and spring 53 may be integrally formed. Spring clip 52 and/or spring 53 may be positively aligned and/or supported by a notch 62 defined in proximal end 51c of circuit board 51. Circuit board 51 includes one or more through holes 56 defined therein that may be utilized to form a conductive pathway between upper surface 51a and lower surface 51b of circuit board 51.

Figure 15:
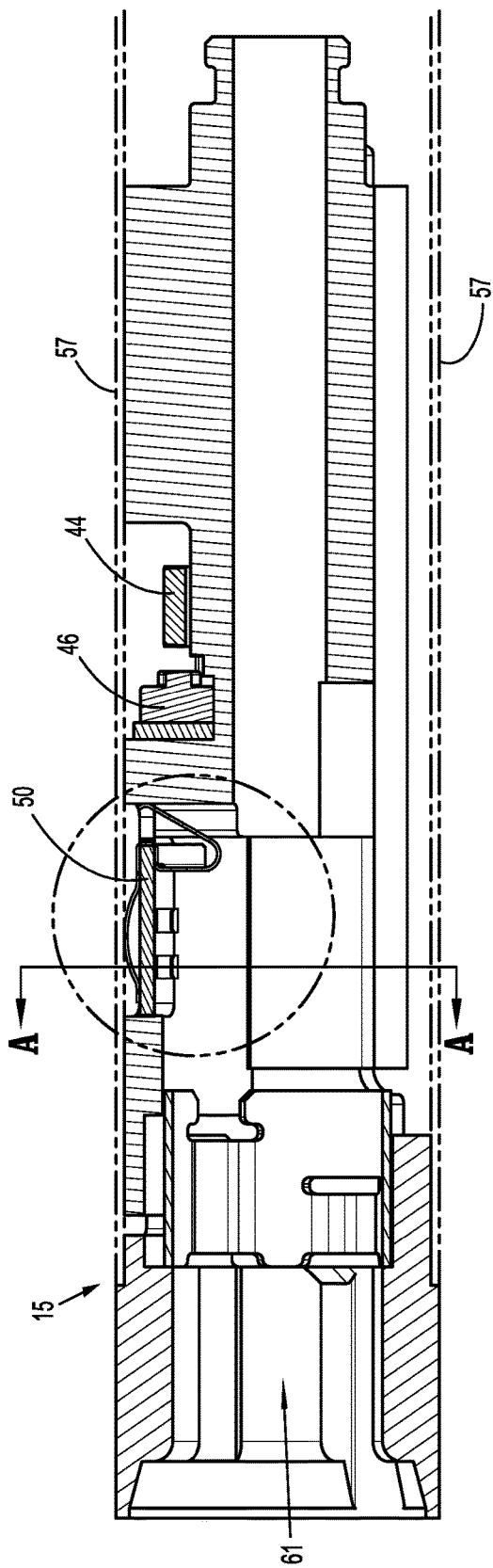
FIG. 15 is a cross-sectional, side view of the adapter assembly shown in FIG. 3 showing the adapter assembly separated from the loading unit.
Figure 16:
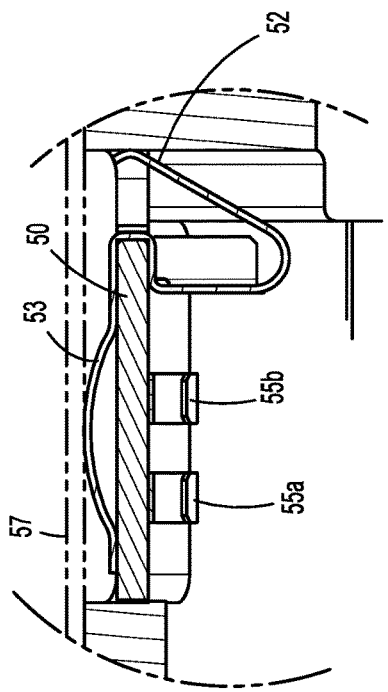
FIG. 16 is an enlarged view of the indicated area shown in FIG. 15 showing the adapter board separated from the authentication board.

When adapter board assembly 50 is mounted within pocket 60, spring 53 bears against outer tube 57 of adapter assembly 14 (FIGS. 15, 16). In use, adapter board 50 is spring-biased towards authentication board assembly 30 by spring 53 and by side spring clip 52 such that, upon joining loading unit 16 and adapter assembly 14, any manufacturing tolerances between loading unit 16 and adapter assembly 14 are compensated for by engagement of the floating spring mount of adapter board 50 within pocket 60. In this manner, a reliable connection between contact members 55 of adapter board 50 and contact members 40 of authentication board assembly 30 is consistently achieved, thus providing a robust communication link between chip 36 and handle assembly 12. In embodiments, contact assembly 38, contacts 40, and/or contacts 55 are formed at least in part from electrically conductive material, such as, without limitation, beryllium copper.

Figure 19:
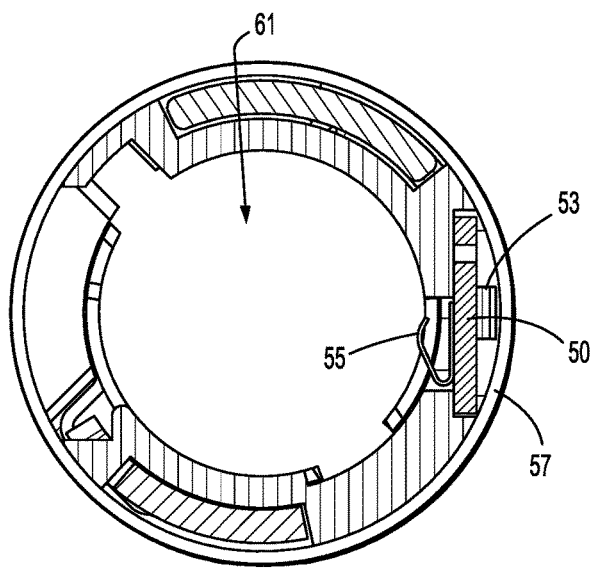
FIG. 19 is a cross-sectional, axial view of the adapter assembly shown in FIG. 3 showing the adapter assembly separated from the loading unit.
Figure 20:
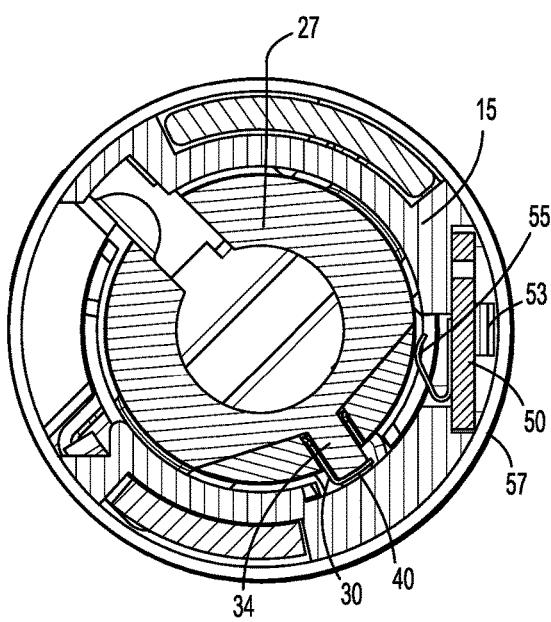
FIG. 20 is a cross-sectional, axial view of the adapter assembly shown in FIG. 3 showing the loading unit inserted into the adapter assembly.
Figure 21:
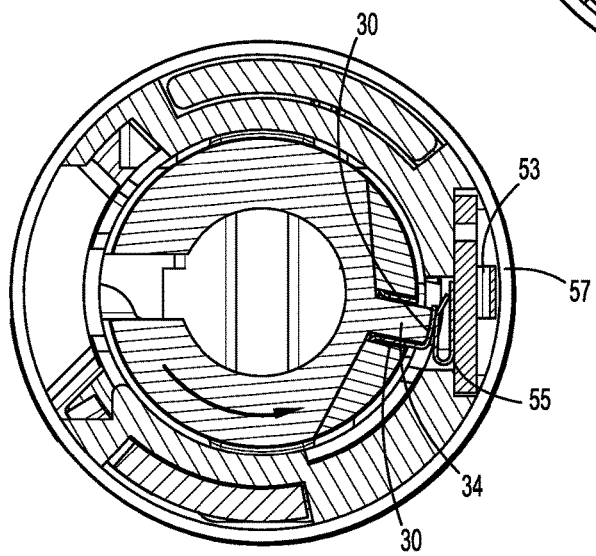
FIG. 21 is a cross-sectional, axial view of the adapter assembly shown in FIG. 3 showing the loading unit engaged with the adapter assembly.
Figure 22:
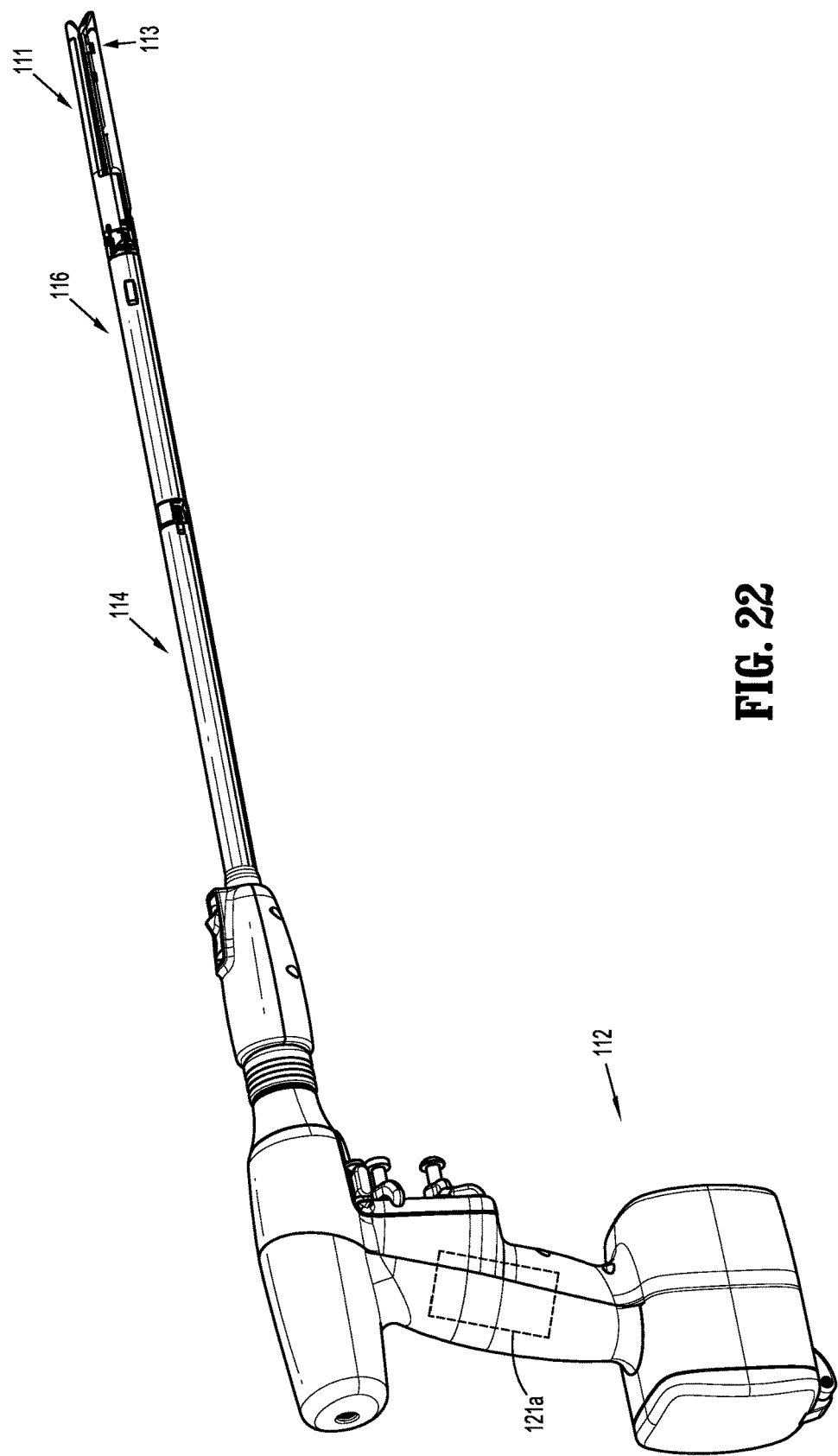
FIG. 22 is a perspective view of a surgical stapling device according to further embodiments of the present disclosure.
Figure 23:
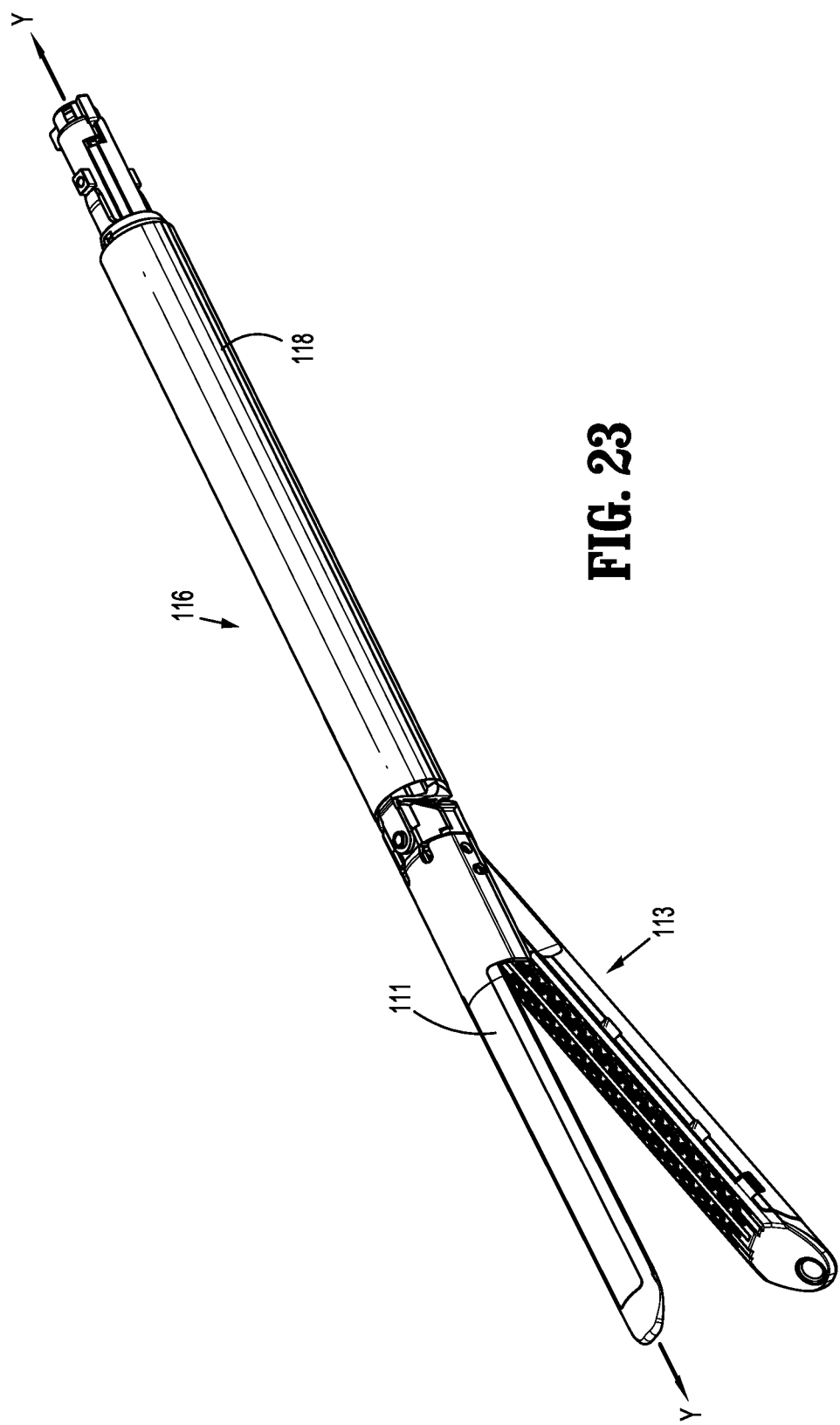
FIG. 23 is a perspective view of a loading unit according to embodiments of the present disclosure.
Figure 24:
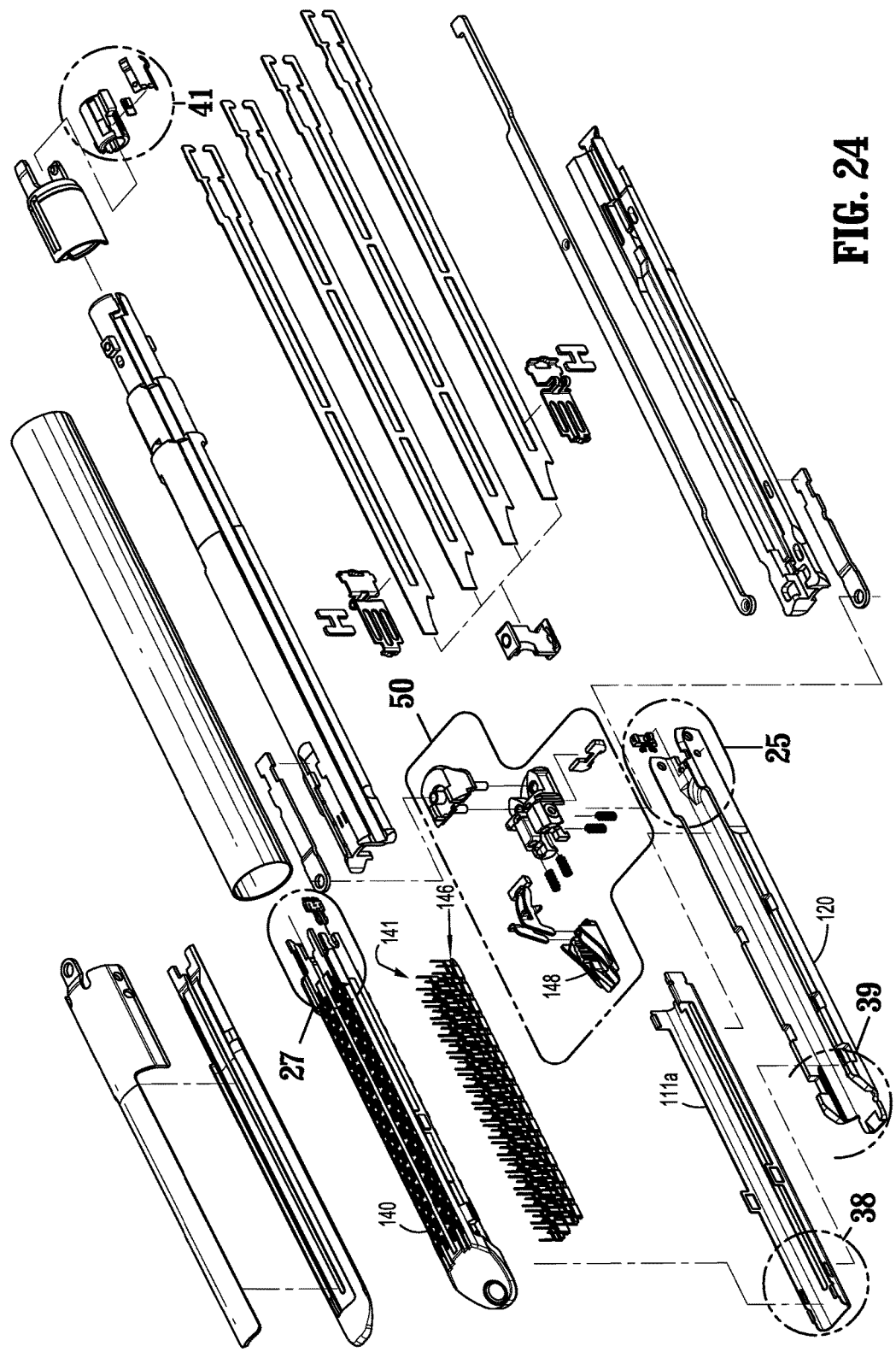
FIG. 24 is the loading unit of FIG. 23 shown with parts separated.
Figure 25:
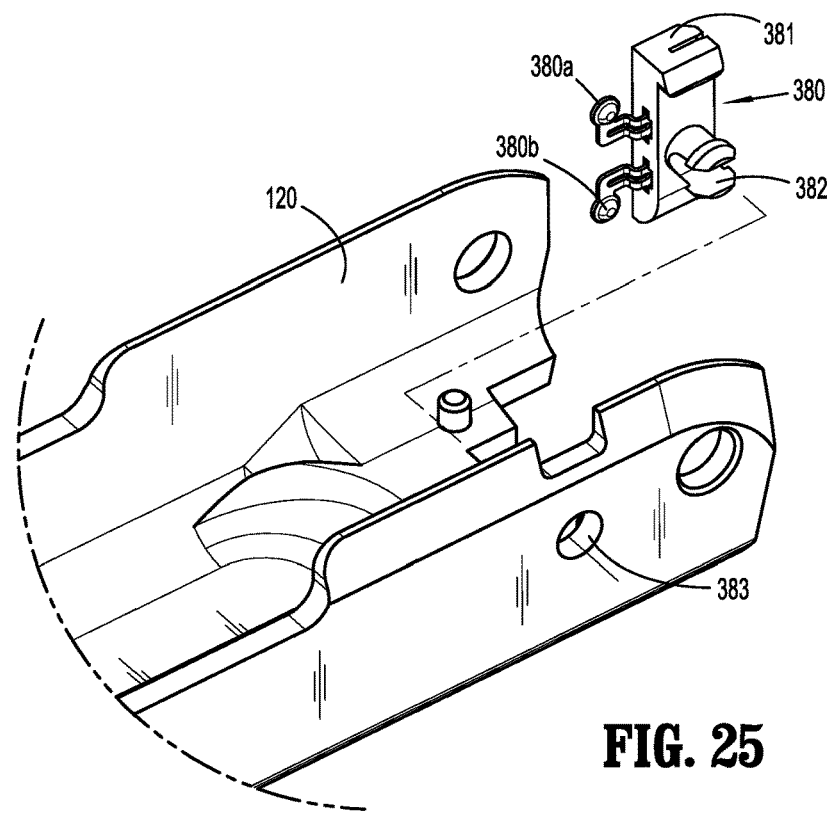
FIG. 25 is a detailed perspective view of a board assembly.
Figure 26:
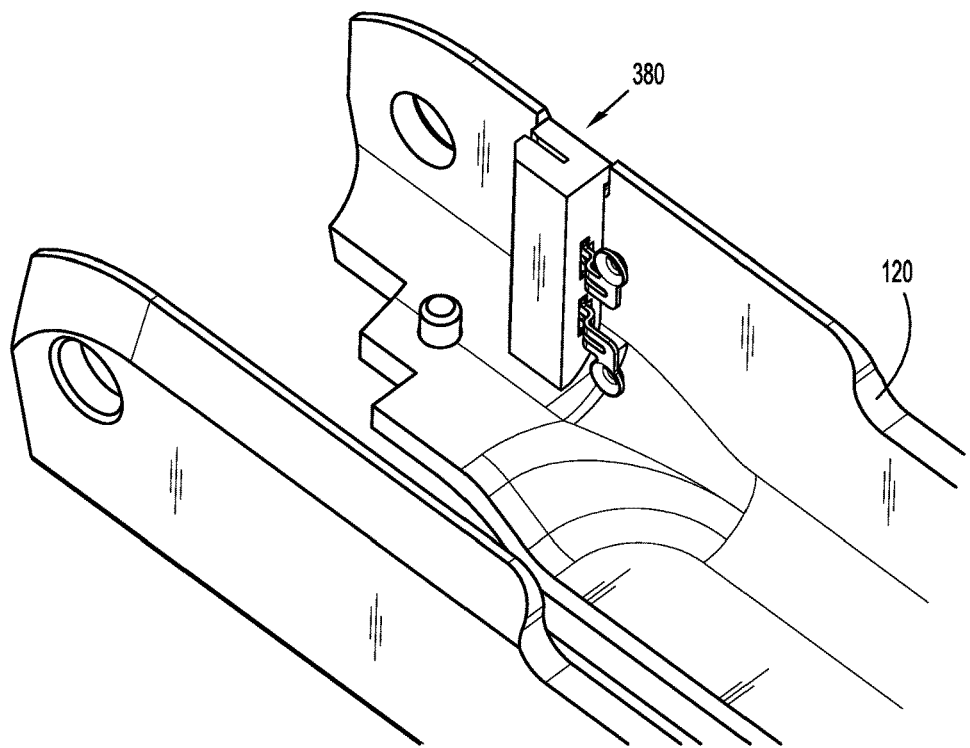
FIG. 26 is a another detailed perspective view of the board assembly of FIG. 25.

Turning now to FIGS. 15-21, the interaction between adapter board assembly 50 and authentication board assembly 30 is shown. As seen in FIGS. 15, 16, and 19, adapter board 50 is retained within loading unit adapter 15 by spring clip 52. Spring 53 bears against outer tube 57 to bias adapter board 50 inwardly towards bore 61, such that contact members 55 extend into bore 61. As adapter coupler 27 is inserted fully into bore 61 of loading unit adapter 15, the initial rotational orientation of adapter coupler 27 and loading unit coupler 15 is such that contact members 40 of authentication board 30 and contact members 55 of adapter board 50 are roughly 45° apart (FIG. 20). As loading unit 16 is rotated with respect to adapter assembly 14, contact members 40 of authentication board 30 are brought into engagement with contact members 55 of adapter board 50. Advantageously, contact support 34 of adapter coupler 27 of loading unit 16 provides radial support to contact members 30 as they engage mating contact members 55 of adapter board 50. In addition, spring 53 bears against outer tube 57 which enables adapter board 50 to float with respect to authentication board 30 and loading unit coupler 15, thereby compensating for manufacturing variations between the various components and providing a reliable connection between authentication board 30 and adapter board 50.

It is contemplated that a loading unit like loading unit 16 could have a removable and replaceable staple cartridge assembly. A stapling system is shown in FIGS. 22-57, in accordance with an embodiment of the present disclosure, having a powered handle assembly 112 similar to the handle assembly 12 discussed above. The handle assembly is configured as discussed above and has a controller 121a. The stapling system includes an adapter assembly 114 and a loading unit 116, each of which can be configured as discussed above. The loading unit is a linear stapling loading unit, but other types of loading units are contemplated. The loading unit 116 has a drive assembly for firing staples into tissue clamped between the anvil jaw member 111 and staple cartridge jaw member 113, as discussed above.

Supported in the staple cartridge jaw member 113 is a removable and replaceable staple cartridge assembly 115. A removable and replaceable staple cartridge assembly is disclosed in U.S. patent application Ser. No. 13/280,880, filed Oct. 25, 2011, and published as US 2013-0098965 A1, the entire disclosure of which is hereby incorporated by reference herein.

Loading unit 116 of the present disclosure is configured to be used more than once. In particular, the loading unit has the removable staple cartridge assembly 115 that includes the staple cartridge and drive assembly discussed above. The removable assembly 116 is configured to be removed and replaced (e.g., after firing staples or other surgical fasteners therefrom). The loading unit 116 shown includes a proximal body portion 118 that is attachable to the adapter assembly 114. However, the features of the loading units of the present disclosure can be incorporated in a surgical instrument in which does not include a detachable portion of the elongated portion of the instrument.

Loading unit 500 includes a proximal body portion 118 defining a longitudinal axis "A-A". Jaw members include an anvil jaw member 111 and a cartridge jaw member 113. One of the jaw members is pivotal in relation to the other to enable the clamping of tissue between the jaw members. In the illustrated embodiments, the cartridge jaw member 113 is pivotal in relation to the anvil jaw member and is movable between an open or unclamped position and a closed or approximated position. However, the anvil jaw member, or both the cartridge and anvil jaw member, can be movable. As discussed in connection with FIGS. 1-21, the anvil jaw member includes an anvil having a plurality of staple forming depressions.

The cartridge jaw member 113 includes a channel or carrier 120 which receives and supports the staple cartridge assembly 115. The cartridge assembly has a cartridge body 140 and a support plate 111. The cartridge body and support plate are attached to the channel or carrier 120 by a snap-fit connection, as discussed below, a detent, latch, or by another type of connection. The cartridge assembly includes fasteners or staples 141. Cartridge body 140 defines a plurality of laterally spaced staple retention slots 142, which are configured as openings (see FIG. 32). Each slot is configured to receive a fastener or staple therein. Cartridge assembly also defines a plurality of cam wedge slots which accommodate staple pushers 146 and which are open on the bottom to allow the actuation sled 148 to pass longitudinally therethrough in the firing of the staples as discussed above.

The removable staple cartridge assembly 115 includes cartridge body 140 and support plate 111. The removable assembly 115 is removable from channel 120, e.g., after staples have been fired from the cartridge body 140. Another removable and replaceable staple cartridge assembly is capable of being loaded into the channel, such that the loading unit 116 can be actuated again to fire additional fasteners or staples.

Channel 120 includes one or a pair of engagement structures 120a (such as slots) for engaging the staple cartridge assembly and support plate (see FIG. 39), a central slot for the passage of the drive beam, a pair of proximal holes 150 for connection with the anvil jaw member, and a ramped surface 152. Proximal holes 150 are configured to align with/mechanically engage a pair of corresponding holes or features on the anvil jaw member. The jaw members can be connected by pins, for example, to facilitate a pivotal relationship between anvil jaw member 111 and cartridge jaw member 113.

Figure 32:
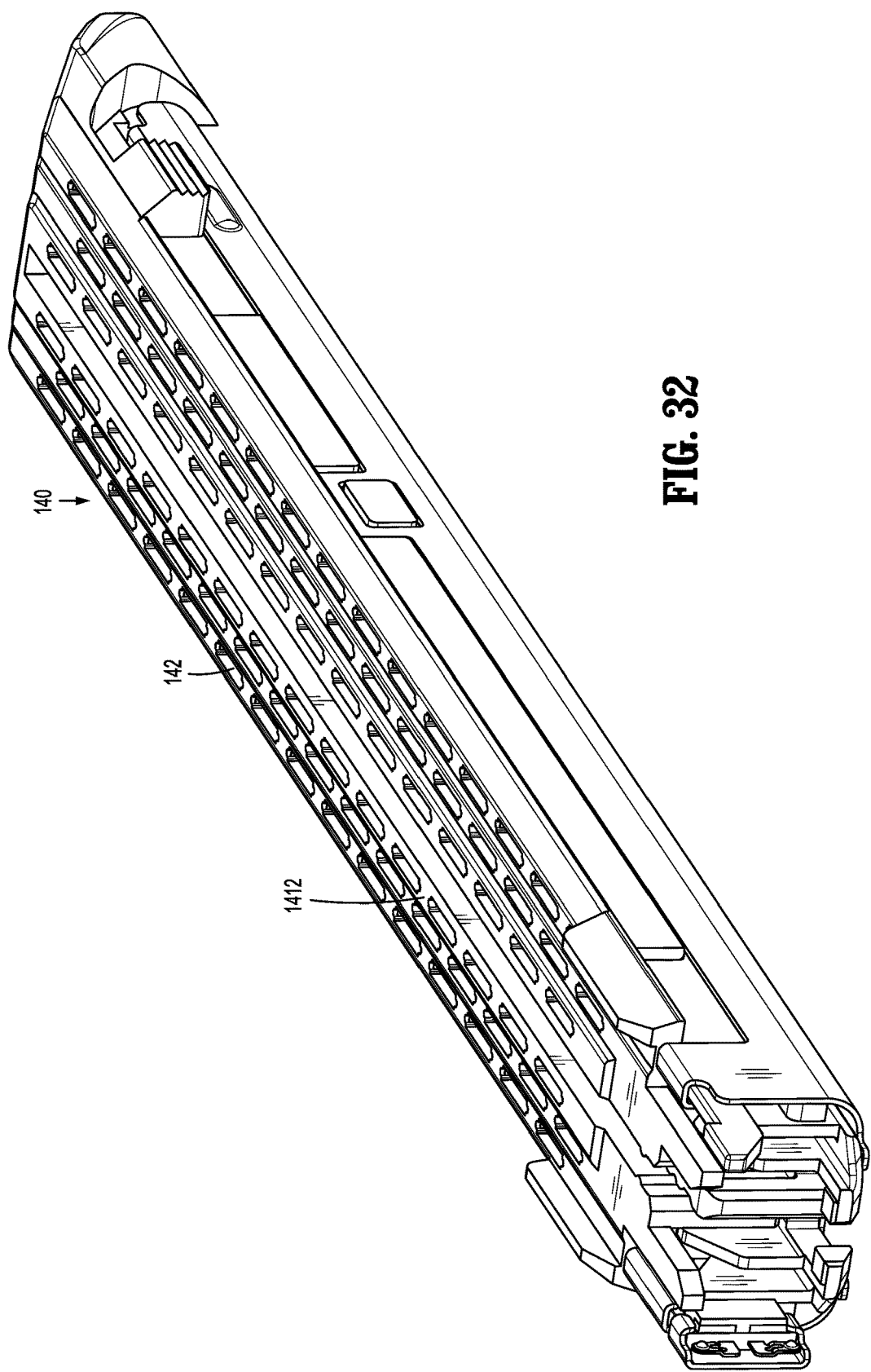
FIG. 32 is a top perspective view of a staple cartridge assembly in accordance with embodiments of the present disclosure.
Figure 38:
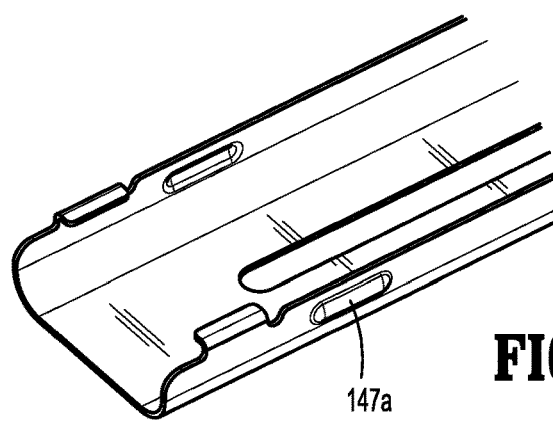
FIG. 38 is a perspective view of the proximal portion of a support plate of the staple cartridge assembly.
Figure 39:
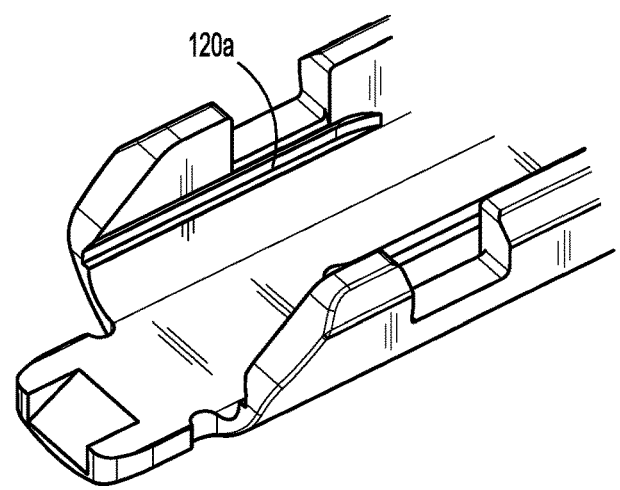
FIG. 39 is a perspective view of the proximal portion of a channel of the loading unit.
Figure 40:
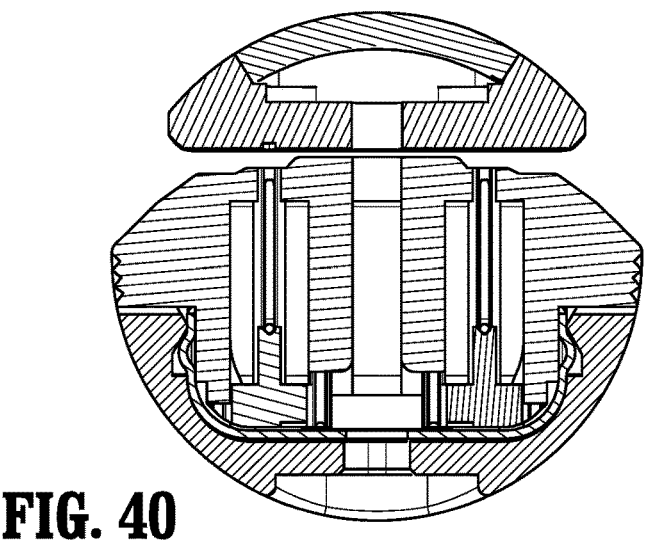
FIG. 40 is a cross sectional view of the loading unit.
Figure 41:
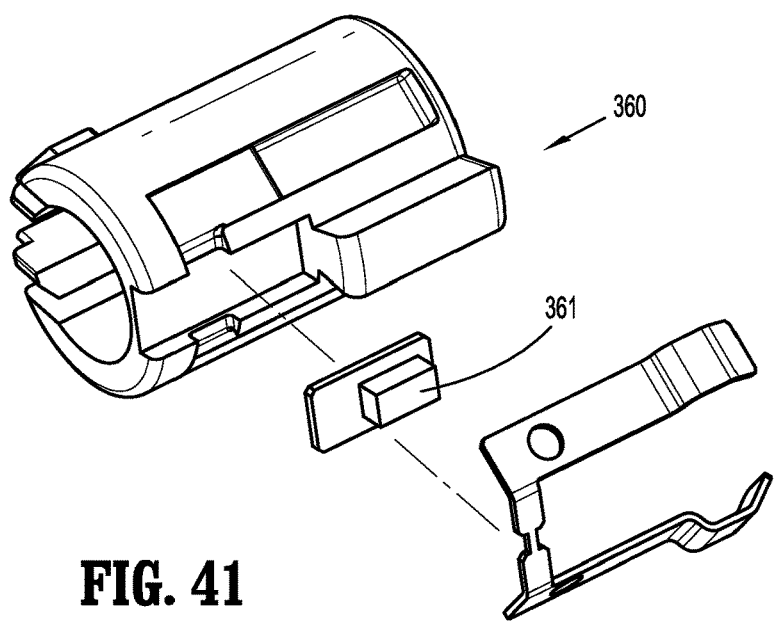
FIG. 41 is a perspective view of a chip assembly of the loading unit with parts separated.
Figure 42:
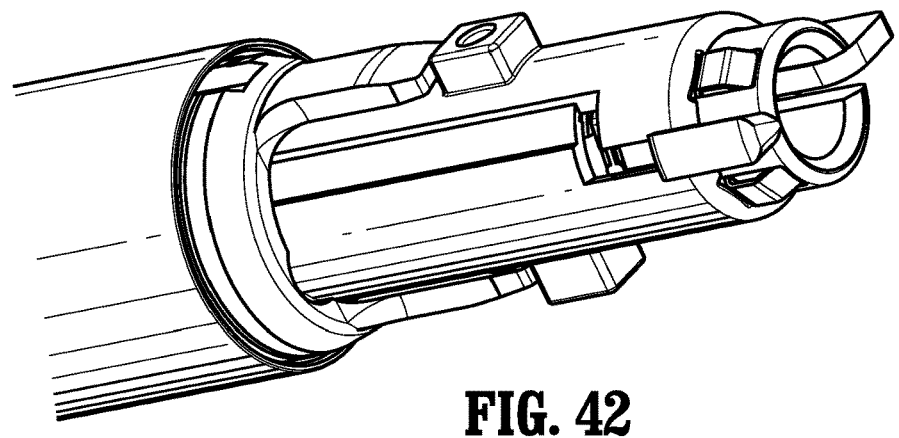
FIG. 42 is a perspective view of the proximal portion of the loading unit.
Figure 43:
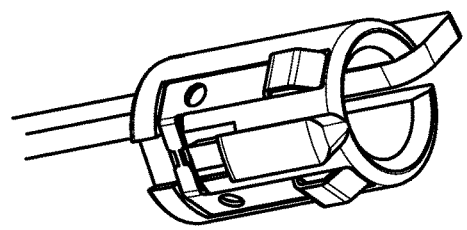
FIG. 43 is a perspective view of the chip assembly.
Figure 44:
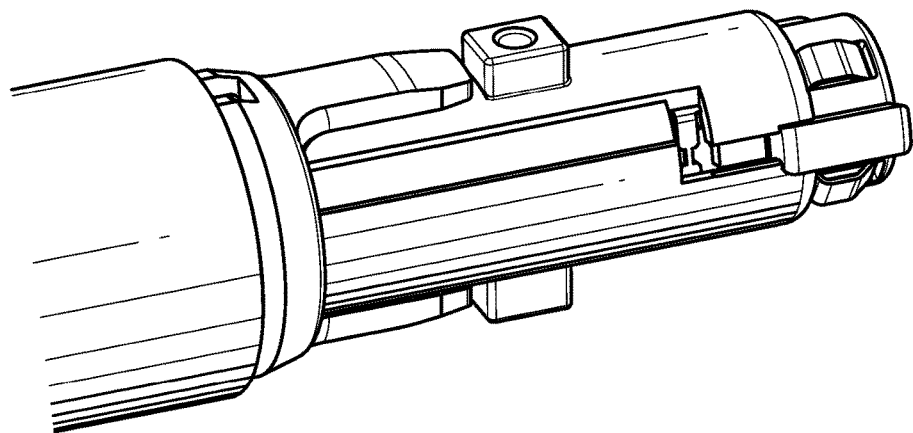
FIG. 44 is a perspective view of the proximal portion of the loading unit.
Figure 45:
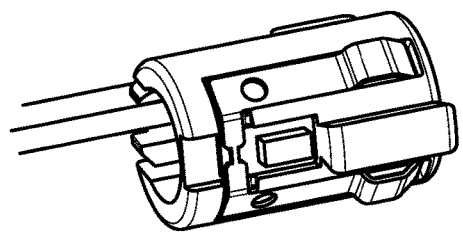
FIG. 45 is another perspective view of the chip assembly.
Figure 46:
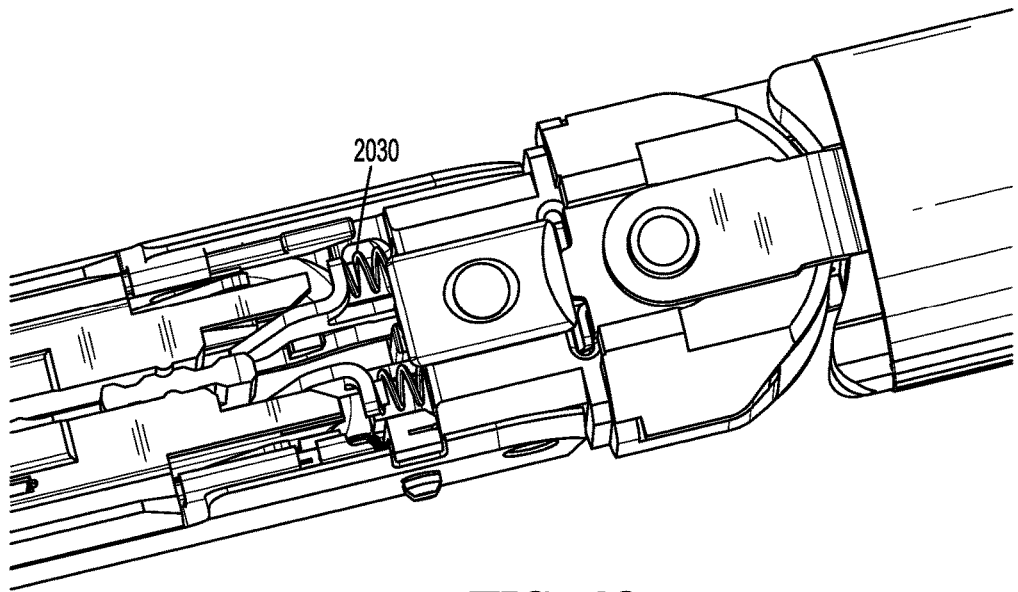
FIG. 46 is a detailed perspective view of a lockout assembly in accordance with embodiments of the present disclosure.
Figure 47:
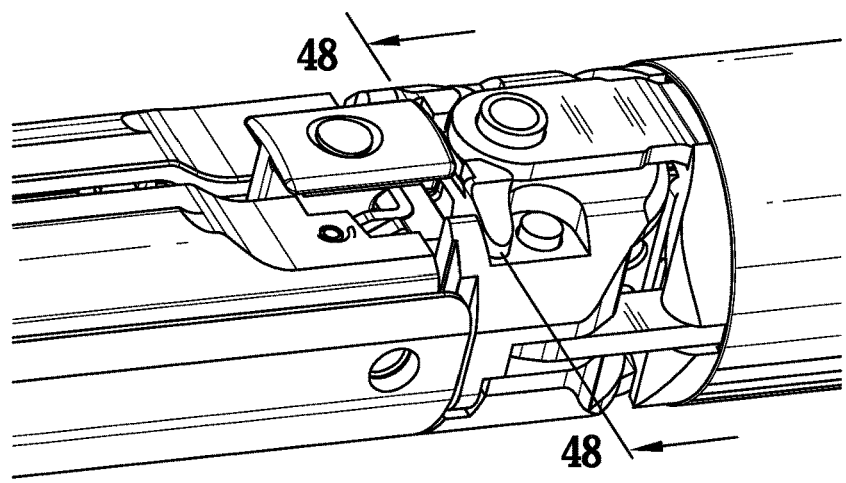
FIG. 47 is another detailed perspective view of a lockout mechanism in accordance with embodiments of the present disclosure.
Figure 48:
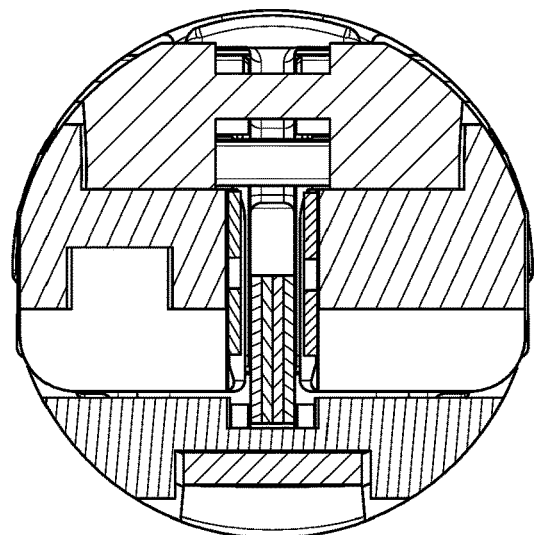
FIG. 48 is a cross sectional view through the drive beam.
Figure 49:
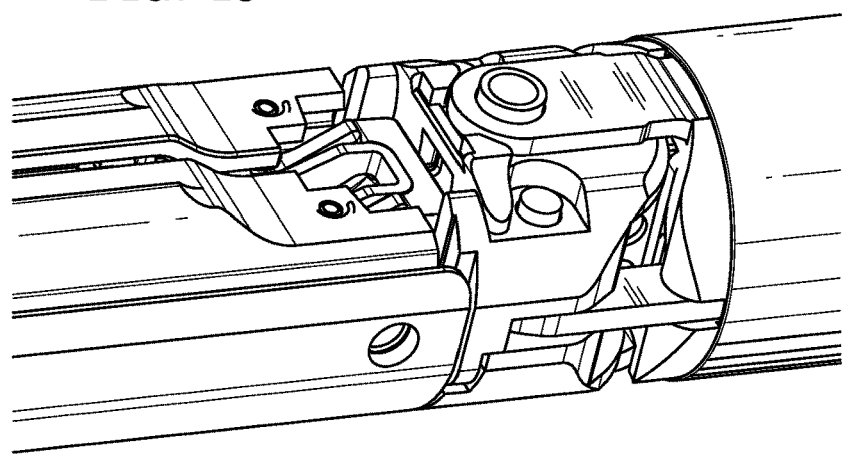
FIG. 49 is a another detailed perspective view of the lockout mechanism.
Figure 50:
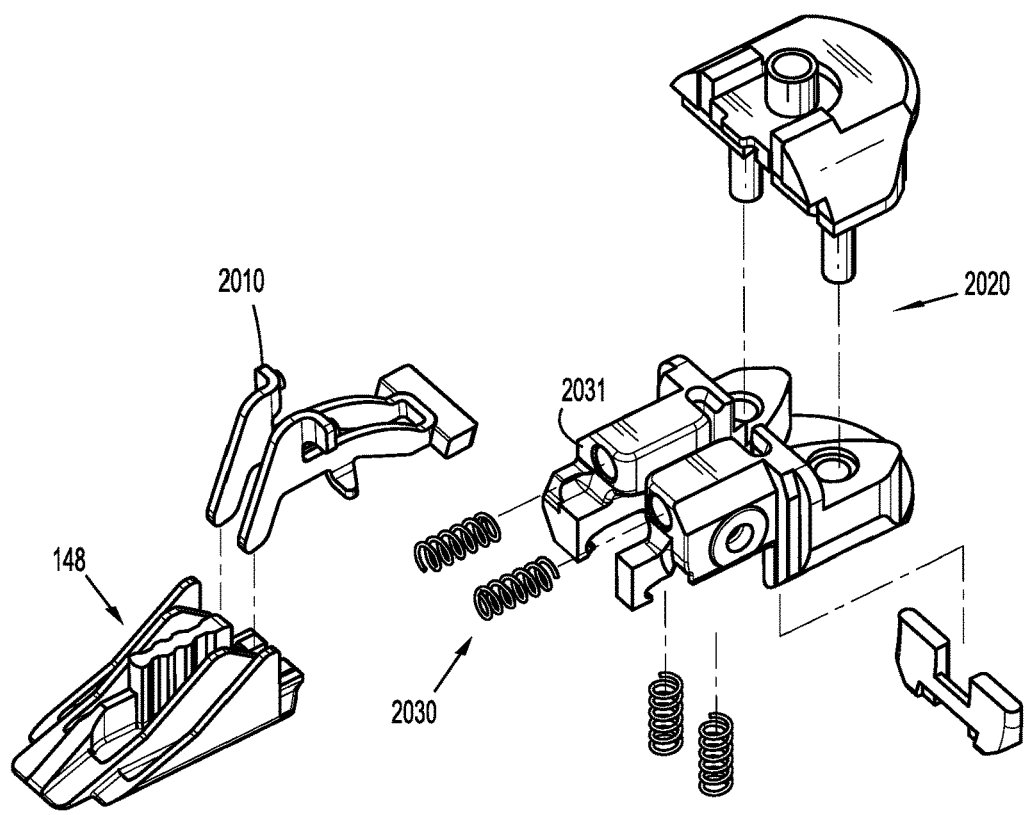
FIG. 50 is a perspective view with parts separated showing a latch, sled, and mounting portion.
Figure 51:
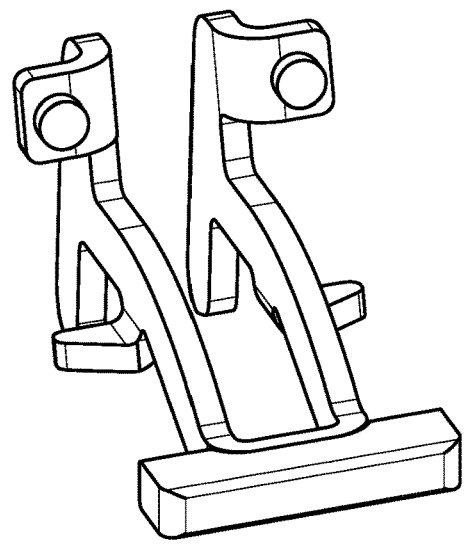
FIG. 51 is a perspective view of the latch.
Figure 52:
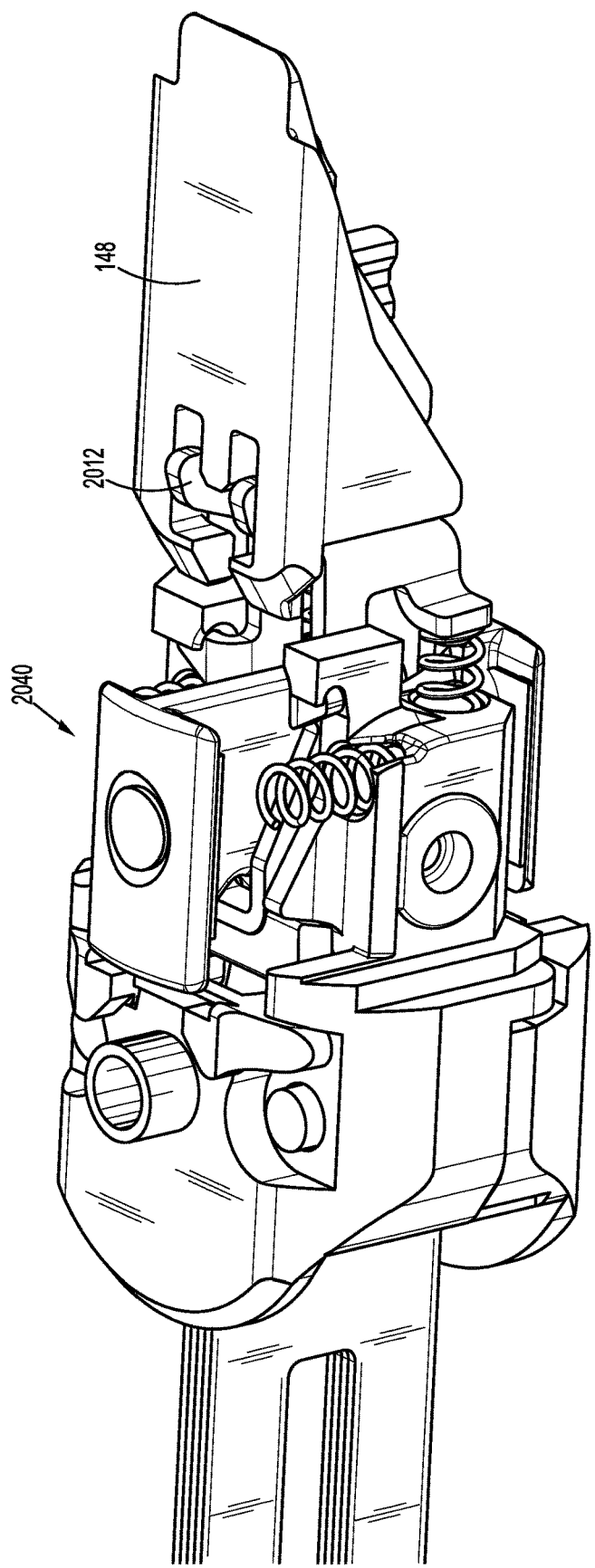
FIG. 52 is a perspective view of the loading unit with parts removed showing the lockout mechanism.
Figure 53:
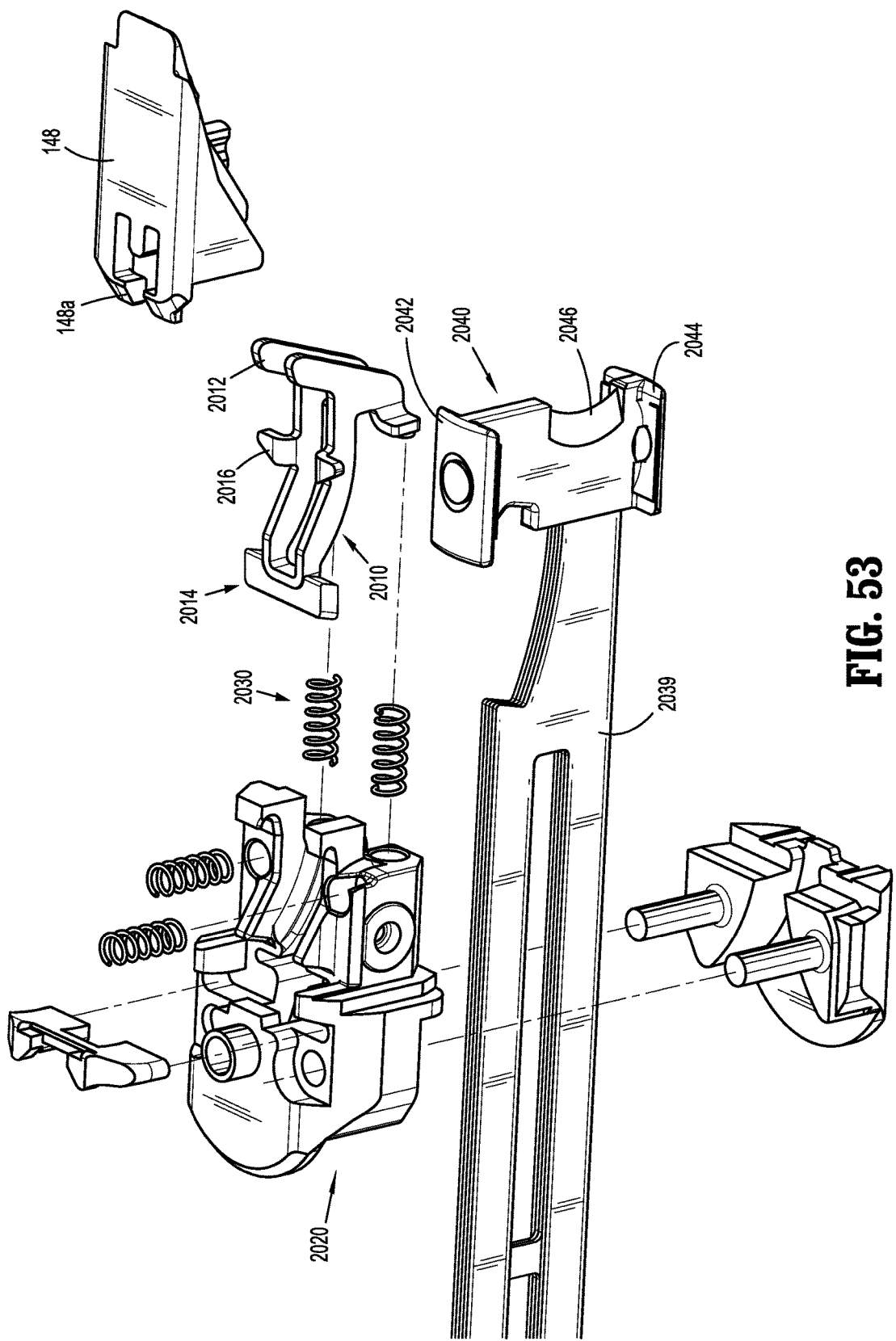
FIG. 53 is a perspective view of the lockout mechanism with parts separated showing the drive beam.
Figure 54:
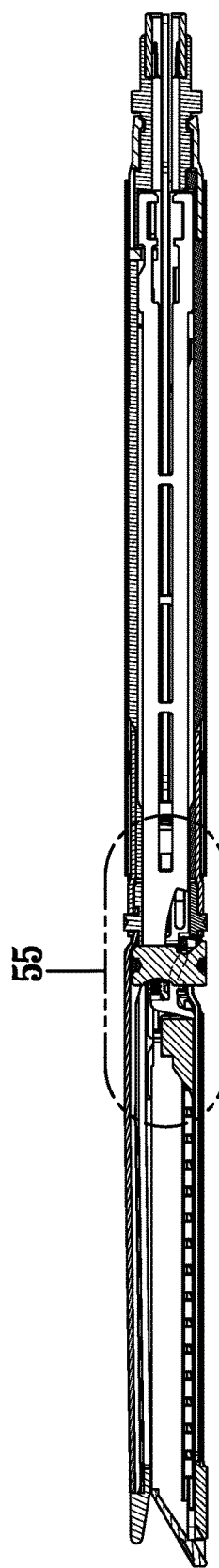
FIG. 54 is a cross sectional view taken longitudinally through the loading unit.
Figure 55:
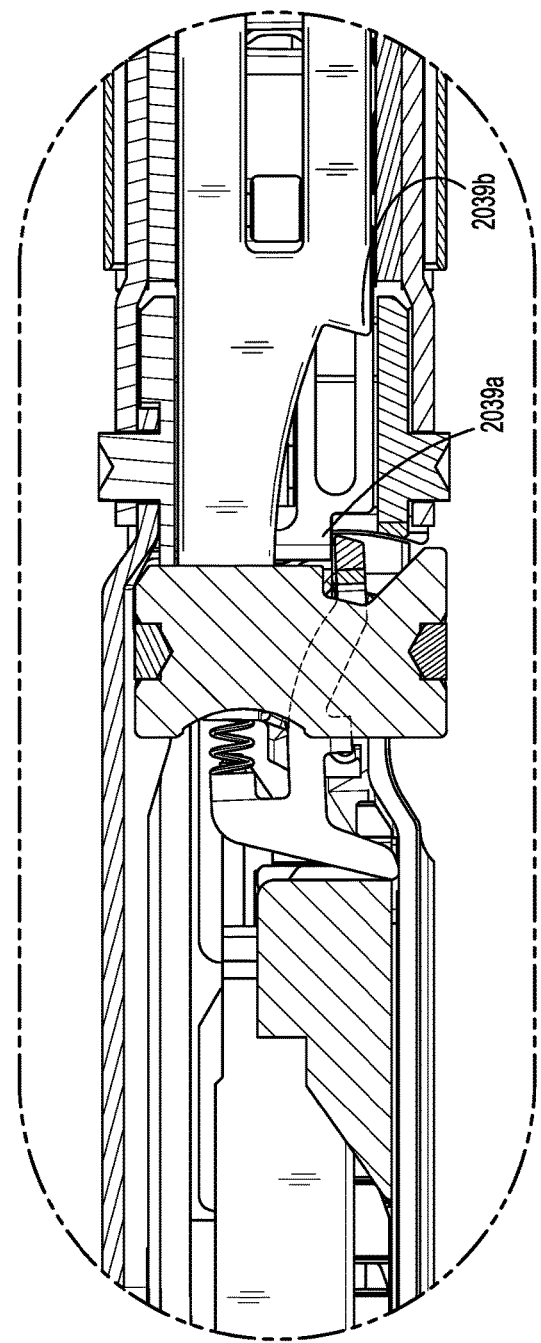
FIG. 55 is a detailed view of FIG. 54 showing the latch and dynamic clamping member.

The cartridge body 140 includes a central slot 143, and rows of staple retention slots positioned on each side of slot 143 (see FIG. 32). Cartridge body also includes a pair of engagement structures or protrusions which may, in certain embodiments, be slots or openings adjacent its proximal end for connection with the support plate 111a and/or channel 120.

Figure 29:
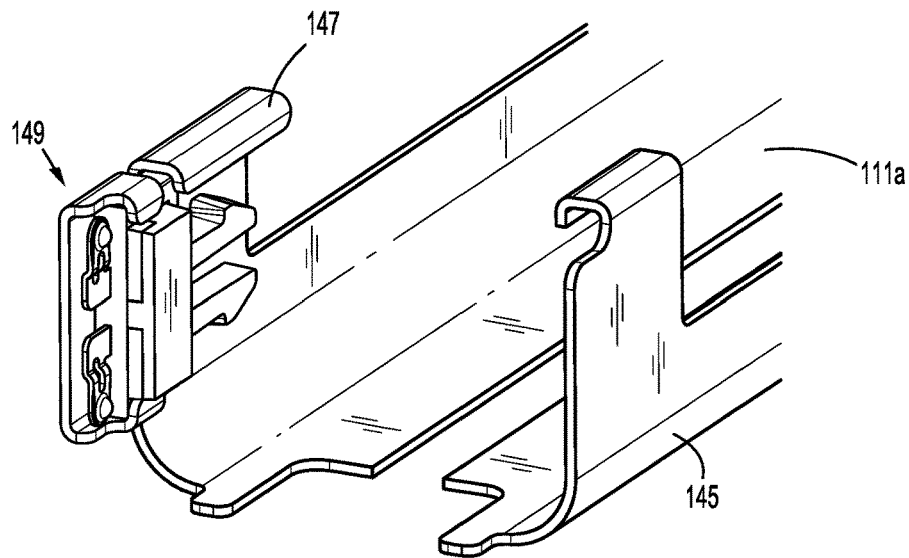
FIG. 29 is a detailed perspective view of a support plate in accordance with embodiments of the present disclosure.
Figure 30:
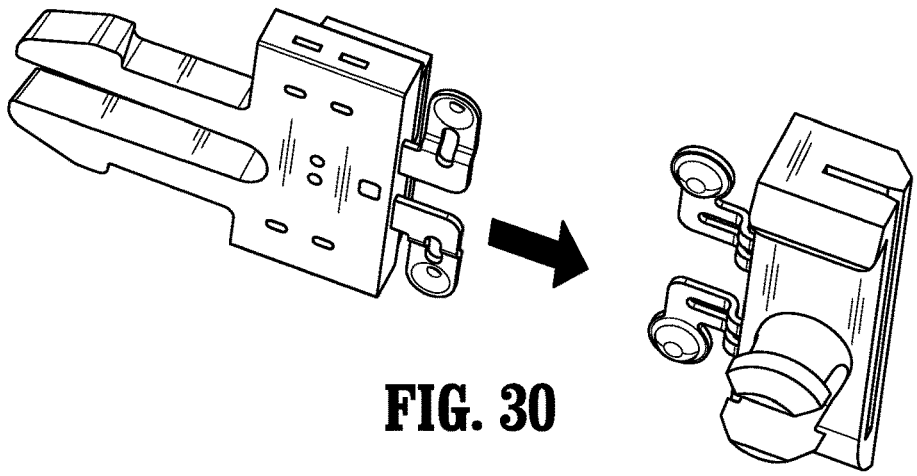
FIG. 30 is a perspective view of the chip assembly and board assembly of FIGS. 25-28.
Figure 31:
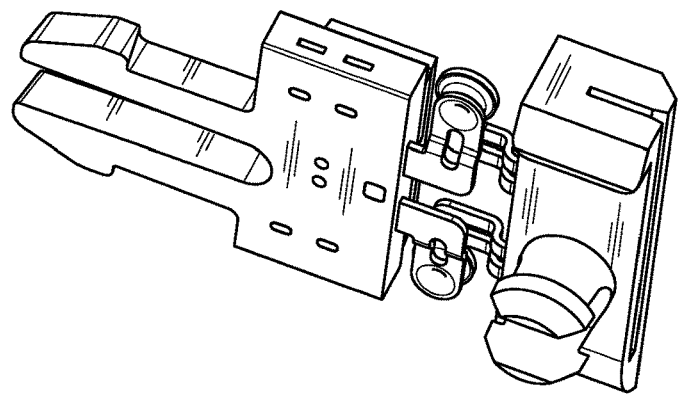
FIG. 31 is another perspective view of the chip assembly and board assembly of FIGS. 25-28.

With particular reference to FIG. 29, support plate 111a includes a base 145, engagement features 147 and 147a (see FIG. 38) for connection with the cartridge body and/or channel, and a mounting portion 149 at a proximal end thereof (see FIG. 29). The support plate 111a is disposed underneath the cartridge body to support the staple pushers, actuation sled, and staples (or other surgical fasteners) and prevent those components from falling out of the staple cartridge assembly.

The loading unit can include a chip assembly 360 mounted on a proximal end of the proximal body portion 118, as shown in FIGS. 41-45, for example. The chip assembly is as described above in connection with the authentication board assembly 30 discussed above. The chip assembly 360 is mounted for connection with a board assembly in the coupler on the distal end of the adapter assembly 114, and can be configured as discussed above in connection with FIGS. 1-21. The chip assembly 360 includes a chip 361 for authentication and information purposes, and can include a memory that stores certain information. The information can include the type of device the loading unit is, the version of the device/loading unit, the name of the loading unit, the manufacturing lot number, the serial or other identification number, the maximum force to which the drive beam of the loading unit can be driven, the interlock zone (mm), the end zone (mm), whether or not the loading unit can articulate, and/or a usage limit (the number of times the loading unit can be used). The interlock zone is the position of the drive beam, in millimeters, measured from the start or initial position of the drive beam, when the drive beam is engaged by a lockout in the loading unit. The end zone is the position of the drive beam, in millimeters, measured from the start or initial position of the drive beam, when the drive beam has reached the end of its travel in the staple cartridge body 140. Since the staple cartridge assembly 115 can be removed and replaced, there is an intended limit to the number of times the loading unit can be reloaded with a fresh unfired staple cartridge. The information stored on the chip can include the staple line length and/or length of the staple cartridge.

The controller 121a in the handle assembly 112 can be programmed to read the information on the chip 361. This information is used in the operation of the surgical system. Desirably, some or all of the information is encrypted, which can be accomplished as discussed above in connection with FIGS. 1-21. The controller can be programmed to not provide power to a motor (not shown) disposed in the handle assembly 112, and not operate the adapter assembly and loading unit, in the event that the serial number or other data is not recognized. The maximum force information is used in conjunction with a load sensor, such as a strain gauge, disposed in the surgical system. For example, a load sensor can be disposed in the adapter assembly 114 and/or loading unit, such as a load sensor on the drive beam. The controller is programmed to compare the data from the load sensor to the maximum force data stored on the chip so that, for example, the operation of the motor (not shown) is interrupted before the maximum force is exceeded. In another example, the controller can be programmed to operate in "slow mode" if the measured force reaches a predetermined level. The predetermined level of force can be the maximum force discussed above, or another level of force, stored on a chip in the system, such as chip 361. Slow mode means that the controller operates the motor (not shown) at a slower rate, generating more torque, and also delaying the compression of tissue and/or firing of staples. In thick tissue, slow mode can allow fluid in the tissue to move away from the site of stapling, facilitating more compression of the tissue.

In a similar manner, the operation of the motor can be stopped or operated in slow mode if the drive beam is disposed in the interlock zone or the end zone. Furthermore, the controller can interrupt or prevent the operation of the articulation linkage, bar or cable if the data on chip 361 indicated that the loading unit does not articulate.

It is contemplated that the chip 361 with some or all of the data discussed above can be provided in any of the embodiments disclosed herein, including loading units that do not have a removable and replaceable staple cartridge assembly, and/or loading units that do not articulate.

It is contemplated that the information on chip 361 can be read by the controller in the handle assembly, another chip in the system, or any other computer component in the surgical system.

In any of the embodiments disclosed herein, the controller can write information to the chip on the loading unit. For example, the maximum force that was used to clamp onto tissue, as measured by the load sensor discussed above, the maximum force that was used to fire staples, and/or the position of the drive beam when the drive beam stops advancing, etc. Other information that can be written to the chip 361 includes the location of the drive beam when the device entered into slow mode, the number of times the loading unit has been fired, whether the loading unit has been fired, the type of handle assembly, the serial number of the handle assembly, the type of adapter assembly, and/or the serial number of the adapter assembly. The maximum force to fire staples can be saved along with the position of the drive beam, in any of the embodiments disclosed herein. The information can also be saved in a memory connected to the controller in the handle assembly, other chips in the system, or other computer components of the surgical system.

It is also envisioned, in any of the embodiments disclosed herein, that an end effector or tool assembly is arranged for articulating between a first position where tool assembly is aligned with longitudinal axis "Y-Y," and a second position where tool assembly is disposed at an angle with respect to longitudinal axis "Y-Y." For example, the tool assembly, which includes the anvil jaw member and the cartridge jaw member, may be mounted so as to be pivotable with respect to the proximal body portion 118. The anvil jaw member and cartridge jaw member can be attached to a mounting assembly 2020 (discussed further below), and the mounting assembly can be pivotably connected to the proximal body portion 118. The loading unit 116 includes one or more cables or linkages disposed in the proximal body portion so that when the cable or linkage is displaced, the tool assembly pivots and articulates with respect to the instrument. Further details of providing articulation are described in detail in commonly-owned U.S. Pat. No. 6,953,139 to Milliman et al., the contents of which are hereby incorporated by reference in their entirety. The adapter assembly 114 can include a linkage, bar or cable for enabling the articulation of the tool assembly.

As seen in FIG. 32, for example, any of the embodiments disclosed herein can include a cartridge body 140 having a stepped tissue-contacting surface 1412. In such embodiments, different sized staples, or all the same sized staples, may be used. Further details of a staple cartridge having multiple staple sizes are included in U.S. Pat. No. 7,407,075 to Holsten et al., the entire contents of which are hereby incorporated by reference herein. The staple forming recesses of the anvil, or the staple pushers, or both, can be configured accordingly, to form the staples in the desired shape and size.

Figure 27:
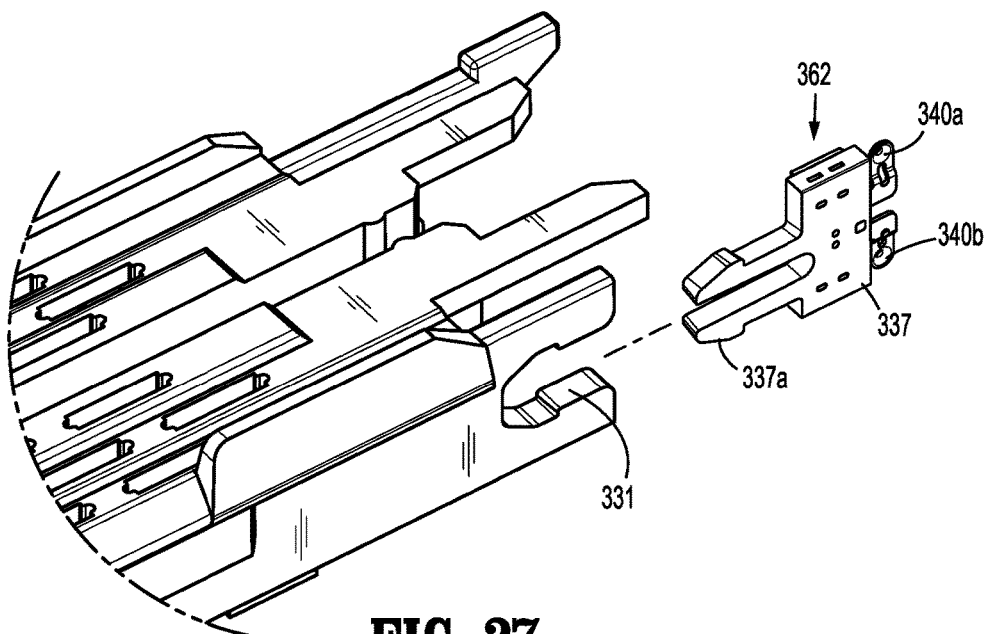
FIG. 27 is a detailed perspective view of a chip assembly.
Figure 28:
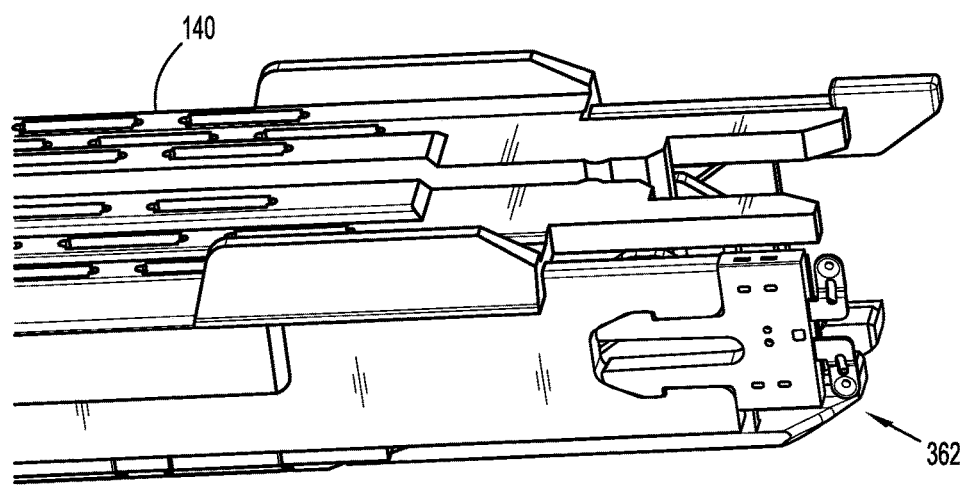
FIG. 28 is another detailed perspective view of the chip assembly of FIG. 27.

The removable and replaceable staple cartridge assembly 115 can further include a chip assembly 362. (see FIGS. 27 and 28). A corresponding board assembly 380 (FIGS. 25 and 26) is disposed on the tool assembly of the loading unit 116, and may be disposed on the channel 120. The tool assembly board assembly 380 can be configured as discussed above in connection with the adapter board assembly 50 of the adapter coupler 27. The tool assembly board assembly 380 is configured to be securely mounted on a wall of the channel 120. This board assembly 380 is positioned such that when cartridge assembly 140 is secured to the channel 120 of the loading unit, the chip assembly 362 engages the board assembly 380 mounted on the channel. (See FIGS. 29-31). FIGS. 27 and 28 show the relationship between the chip assembly and the staple cartridge body 140, whereas FIG. 29 shows the relationship between the chip assembly 362 and the support plate 111a.

In more detail, chip assembly includes a body 337 and a pair of contact members 340a, 340b (collectively, contact members 340) connected to a chip 336 disposed in the body. Body 337 defines a rectangular member having flexible arms with snap features 337a thereon. The flexible arms are configured to be securely received within a recess 331 defined by in the cartridge body. Chip 336 is in electrical communication with contact members 340.

Chip 336 includes any chip capable of storing information concerning the staple cartridge assembly 115. The chip can be the same as or similar to the chip of authentication board assembly 30. In any of the embodiments disclosed herein, any of the chips can store information such as, without limitation, cartridge size, staple arrangement, staple line length (or cartridge length), date of manufacture, expiration date, compatibility characteristics, a unique identifier (e.g., a serial number), and/or number of uses, as well as whether or not the staple cartridge assembly has been used. Such information can be transmitted to the controller in the handle assembly 112, or to another computer component through an appropriate bus, pin connection, wireless means, etc. In some embodiments, chip 336 includes an erasable programmable read only memory ("EPROM") chip. The controller in the handle assembly can write information to the chip 336. In this manner, the handle assembly 112 may adjust the firing forces, firing stroke, and/or other operational characteristics thereof in accordance with the information concerning the staple cartridge assembly that are transmitted from chip 336. The handle assembly 112 can communicate to chip 336 that the staple cartridge assembly has been used, which can prevent reloading or reuse of an expended reload assembly, or any other unauthorized use. The information stored in any of the components in the surgical system can be encrypted using private keys, public keys, and/or secure hash algorithms.

The board assembly 380 also has a pair of contacts 380a and 380b and a body 381. The board assembly is mounted for contact with the chip assembly 362 when the staple cartridge assembly is properly mounted in the channel 120. The contacts 380a, 380b, 340a, and 340b have an L-shaped configuration as seen in the figures so that they may resiliently engage one another. The body 381 can define a snap feature 382 that is provided to engage a hole 383 in the channel to securely mount the board assembly. The board assembly is appropriately connected to a bus, wires, or has a wireless communicator for transmittal of the information from chip assembly 362 to the controller in the handle assembly, or any other computer device.

In any of the embodiments disclosed herein, a lockout mechanism 500 is disposed in the loading unit. The loading unit may be configured as discussed above. Furthermore, the present disclosure is directed to a removable assembly having the lockout, or a loading unit having the lockout.

The lockout mechanism 500 includes a latch 2010 and at least one spring 2030, and is configured to prevent re-firing of a staple cartridge assembly 115 or staple cartridge 26, and also prevent distal translation of a drive beam after the staple cartridge has been fired and prior to loading of another cartridge assembly 115. The lockout mechanism 500 is shown alongside the sled 148 and mounting assembly 2020 in FIG. 50. The at least one spring 2030 is mounted on a distally facing surface 2031. For example, recesses are formed in surface 2031 for receiving springs 2030. Corresponding posts are provided on a proximally facing surface of the latch 2010. The latch is configured to be pivotable within the loading unit, and includes at least one prong 2012, a rear portion 2014, and a supporting portion 2016. The latch is configured to pivot around the supporting portion 2016, shown in FIGS. 50 and 51 as two downwardly depending features, and is biased by the spring or springs 2030. The sled 148 has a hole or recess for receiving the at least one prong 2012 when the latch and drive beam are in their initial positions. (see FIG. 52). The drive beam 2039 can interact with, or include, a dynamic clamping member 2040 having an upper flange 2042, lower flange 2044, and knife blade 2046. (see FIG. 53).

In the initial position, the latch 2010 is biased in a forward or distal direction, with the rear portion 2014 in contact with an edge 2039a on the drive beam 2039, preventing further rotational movement of the latch. As the drive beam and dynamic clamping member are moved in a forward or distal direction, the dynamic clamping member pushes the sled distally. A rear portion 148a of the sled pushes the prong or prongs 2012, tilting the latch against the bias of the at least one spring 2030. This removes the rear portion 2014 from the area near the edge 2039a, and allows the drive beam and dynamic clamping member to move forward. After the dynamic clamping member passes the latch 2010, the latch rotates forwardly under the influence of the spring. (see FIG. 57).

After the dynamic clamping member and sled have fired the staples from the cartridge 140, the dynamic clamping member is moved proximally, leaving the sled at the distal end of the cartridge 140 and cartridge assembly 115. The dynamic clamping member can move past the latch 2010, as cam surface 2041 moves the latch out of the path of travel (see FIG. 57). Once the dynamic clamping member returns to the initial position, the latch 2010 will prevent another forward movement of the dynamic clamping member 2040. The latch rear portion 2014 is in a position to engage another edge 2039b of the drive beam. (see FIG. 57). If the loading unit is of the type that accepts removable and replaceable staple cartridge assemblies 115, the cartridge assembly 115 can be configured to return the latch 2010 to the initial position, so that the drive beam and dynamic clamping member can again be moved distally to fire another set of staples.

As discussed above, any of the embodiments disclosed herein can include a chip assembly 360 on a surgical stapling loading unit, like loading unit 116, that has information on it concerning the lockout mechanism, such as the lockout mechanism discussed above. Furthermore, information can be stored on the chip 361 concerning the lockout mechanism. For example, the fact that the lockout mechanism was engaged can be recorded in chip assembly 360 and/or chip assembly 362 by the controller in the handle. The controller in the handle can include a memory for storing information, including a processor, and other computer components. The controller can also include a current meter, or ammeter, to measure the current in the motor of the handle assembly. The controller can be programmed to record the peak current reached during use of the loading unit and/or staple cartridge assembly, and can record that peak current on any of the chips or other computer components in the system. A peak current reached after the staples have been fired can be an indication that the loading unit was attempted to be fired a second time before a fresh staple cartridge assembly was mounted in the loading unit. Alternatively, the lockout mechanism can include a sensor such as, for example, on the latch. It is contemplated that the surgical system can include loading units that do not have a lockout mechanism like the one discussed above. The fact that the loading unit does not have a lockout mechanism can be stored in chip 361.

The handle assembly can also include an encoder that determines how many rotations of the motor output shaft have been made, which can be used to determine a position of drive bars, linkages, cables, etc., in the adapter assembly, the firing bar in the loading unit, or other components. Alternatively, other sensors can be used to determine the position of various components in the surgical system.

The adapter assembly disclosed herein, in any of the embodiments disclosed herein, can be configured as disclosed in U.S. Published Application No. 2011/0174099 A1, the entire disclosure of which is hereby incorporated by reference herein. The motor in the handle assembly provides a rotational output on a rotating shaft and the adapter is configured to transform that output to a linearly moving linkage or bar, and can also provide drive to an articulation linkage in the proximal body portion 118 of the loading unit 116. The handle assembly and/or adapter assembly can be configured as disclosed in U.S. Published Application Nos. 2014/0012289 A1 and 2014/0110453 A1, the entire disclosures of which are hereby incorporated by reference herein.

Any of the embodiments described in connection with FIGS. 1 through 57 can include the protocol and/or multiplexor discussed herein. In any of the embodiment disclosed herein, the motor in the handle assembly or housing may be any electrical motor configured to actuate one or more drives (such as rotatable drive connectors). The motor is coupled to a battery, which may be a DC battery (e.g., rechargeable lead-based, nickel-based, lithium-ion based, battery etc.), an AC/DC transformer, or any other power source suitable for providing electrical energy to the motor.

Figure 58:
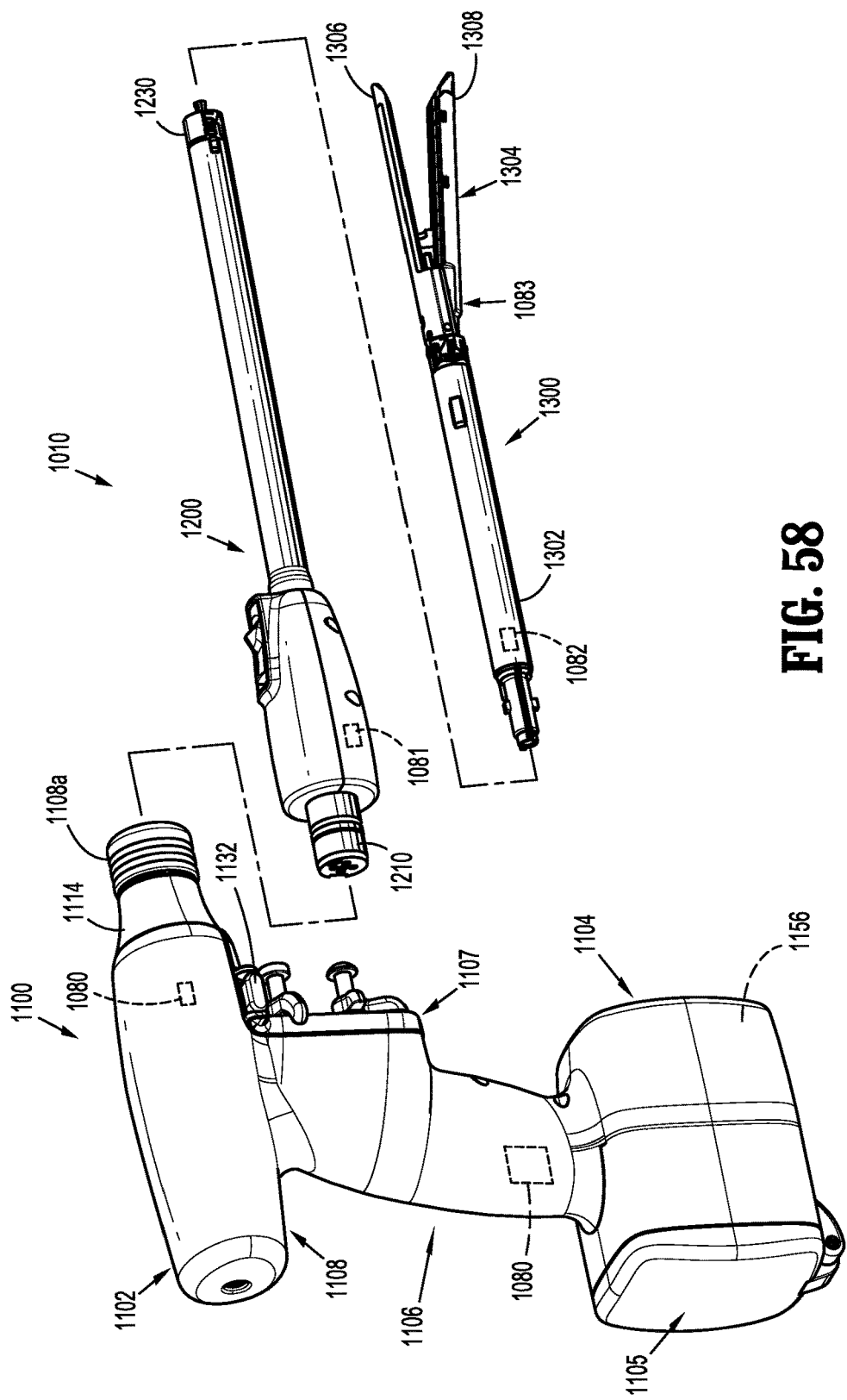
FIG. 58 is a perspective view of a surgical system in accordance with an embodiment of the present disclosure.

FIG. 58 shows a surgical system 1010 including a surgical device 1100 that is selectively connectable to an adapter 1200, in turn, selectively connectable to a surgical loading unit 1300. Such a system is disclosed in U.S. patent application Ser. No. 14/172,109, the disclosure of which is hereby incorporated herein by reference in its entirety. It is contemplated that a variety of surgical reload assemblies 1300 can be used in connection with the system 1010, including electrosurgical reloads, circular stapling loading units, linear stapling loading units, suturing devices, etc.

Adapter 1200 is configured to connect at least one configuration of the surgical reload assembly 1300 to the surgical device 1100, wherein the surgical device 1100 may provide two rotating drive outputs, which can be converted into different rotational drives, linear drives, etc., so that different configurations of the surgical loading units 300 can be operated by the surgical device 1100. As seen in FIG. 58, the adapter 200 generally includes a proximal coupling assembly 1210 at a proximal end thereof and a distal coupling assembly 1230 at a distal end thereof.

Surgical device 1100, as shown in FIG. 58, includes a handle housing 1102 having a lower housing portion 1104, an intermediate housing portion 1106 extending from and/or supported on a lower housing portion 1104, and an upper housing portion 1108 extending from and/or supported on an intermediate housing portion 1106. Handle housing 1102 supports a trigger housing 1107 on a distal surface or side of intermediate housing portion 1108. Upper housing portion 1108 defines a connecting portion 1108a configured to accept a corresponding drive coupling assembly 1210 of adapter 1200. Lower housing portion 1104 of the handle housing 1102 provides a housing in which a battery 1156 is removeably situated. Battery 1156 is configured to supply power to any of the electrical components of the surgical device 1100. Lower housing portion 1104 defines a cavity (not shown) into which the battery 1156 is inserted. Lower housing portion 1104 includes a door 1105 pivotally connected thereto for closing the cavity of the lower housing portion 1104 and retaining the battery 1156 therein.

Surgical loading unit 1300 generally includes a proximal body portion 1302 and a tool assembly 1304. Proximal body portion 1302 is selectively connectable to the distal coupling assembly 1230 of the adapter 1200, and the tool assembly 304 is pivotally attached to a distal end of proximal body portion 1302. Tool assembly 1304 includes an anvil assembly 1306 and a cartridge assembly 1308. In the illustrative embodiment shown in FIG. 58, the surgical loading unit 1300 is a linear stapling reload with a separately removable and replaceable cartridge, and the adapter 1200 is configured to drive the various components of the reload assembly 1300 in order to clamp tissue, fire staples, and cut the tissue. An example of a surgical reload assembly having a removable and replaceable staple cartridge assembly is disclosed in U.S. patent application Ser. No. 13/280,880, the disclosure of which is incorporated herein by reference in its entirety.

Surgical device 1100 includes a controller 1080 that contains the device software that operates the surgical device 1100, the adapter 1200, and/or the surgical loading unit 1300. Connections to the various hardware and software interfaces of the surgical system 1010, and electrical connections relating to the controller 1080, are described in U.S. patent application Ser. No. 13/331,047, the disclosure of which is hereby incorporated herein by reference in its entirety.

The presently-disclosed PCB utilizes a multiplexing scheme and microprocessor to combine 1-wire data and UART (universal asynchronous receiver/transmitter) transmit and UART receive onto a single mechanical pin or other physical connector, so that data can be read from the chips in the various components of the system in an efficient manner. In some embodiments, the chips in each component may be Dallas one wire chips, which have a single data wire and a ground wire The presently-disclosed PCB embodiments require two 2 wires (data and ground), for example, as opposed to four wires required to implement using standard topology. The presently-disclosed communication protocol may increase reliability because there are fewer mechanical parts subject to corrosion and/or failure, particularly where PCB pins may be exposed to blood. The teachings of the present disclosure may apply to a variety of surgical devices that include a bus system.

Figure 59:
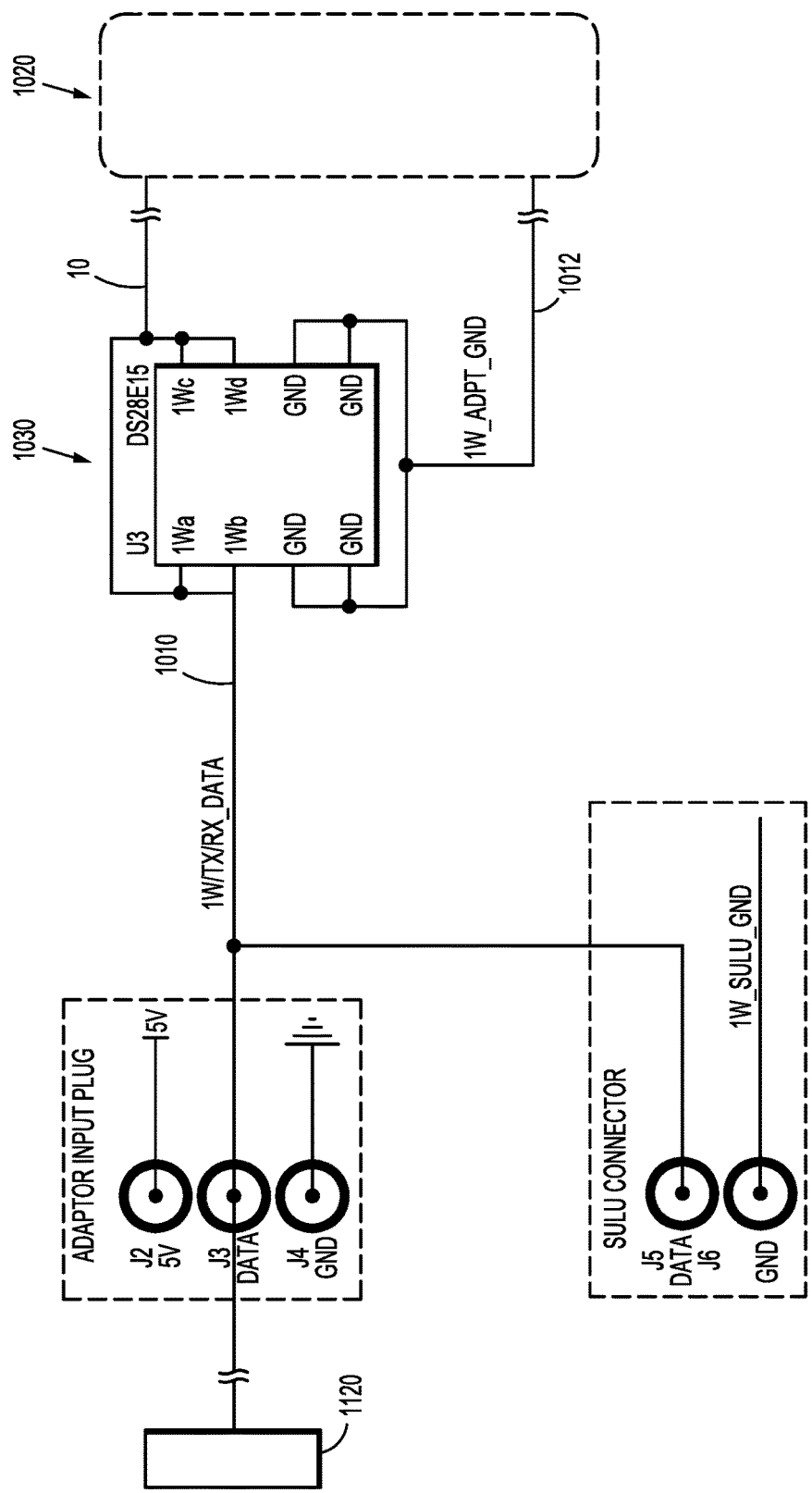
FIG. 59 a circuit diagram of a printed circuit board (PCB) in accordance with an embodiment of the present disclosure.
Figure 60:
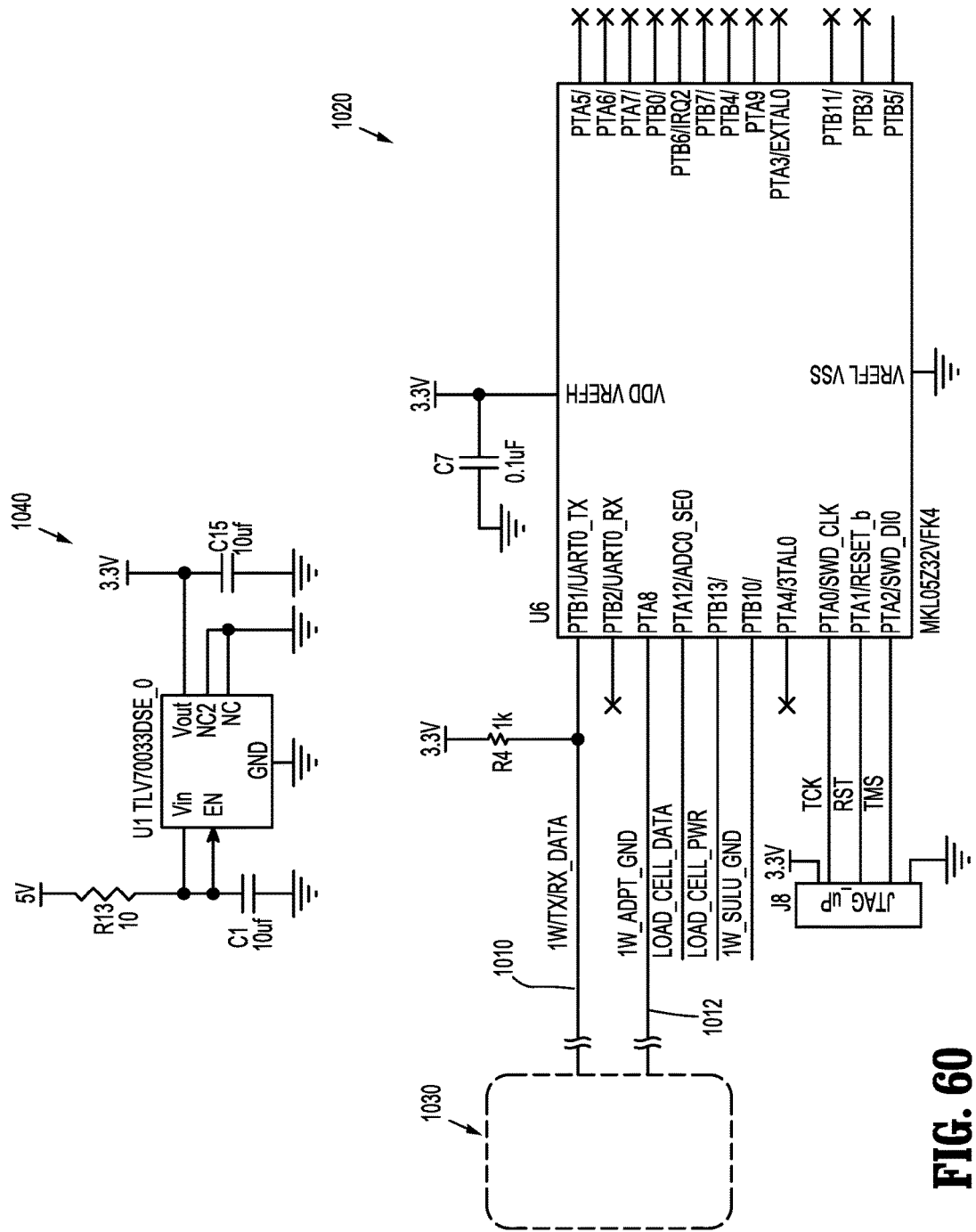
FIG. 60 is a circuit diagram of a PCB in accordance with an embodiment of the present disclosure.

FIGS. 59 and 60 show a PCB that includes a microprocessor 1020, a microchip 1030, and a bus 1010, which is configured to receive signals from a signal source 1120, e.g., controller 1080 of the surgical device 1100. Microchip 1030 is configured to provide device authentication, and may utilize a one-wire data interface. Microchip 1030 is communicatively-coupled through the bus 1010 to the signal source 1120 and communicatively-coupled to the microprocessor 1020. As shown, the microchip is the DS28E15 chip from Maxim Integrated, but other chips may be used. Microprocessor 1020 is capable of demultiplexing transmit and receive lines. It is contemplated that the signal source can be some other computer component, such as an operating room computer system or robotic surgical system.

Based upon communications between microprocessor 1020 and the signal source 1120, the microprocessor 1020 controls bus selection. In some embodiments, a receive mode and a transmit mode over the bus 1010 are controlled by multiplexing on the microprocessor 1020 utilizing a ground wire 1012 of the microchip 1030. In order to transmit over the bus 1010, the ground wire 1012 is turned off, and the microprocessor 1020 selects the transmit mode. In order to receive over the bus 1010, the ground wire 1012 is turned on, and the microprocessor 1020 selects the receive mode.

Hereinafter, a method of communicating data through a bus in accordance with the present disclosure is described with reference to FIG. 60. It is to be understood that the steps of the method provided herein may be performed in combination and in a different order than presented herein without departing from the scope of the disclosure.

Figure 61:
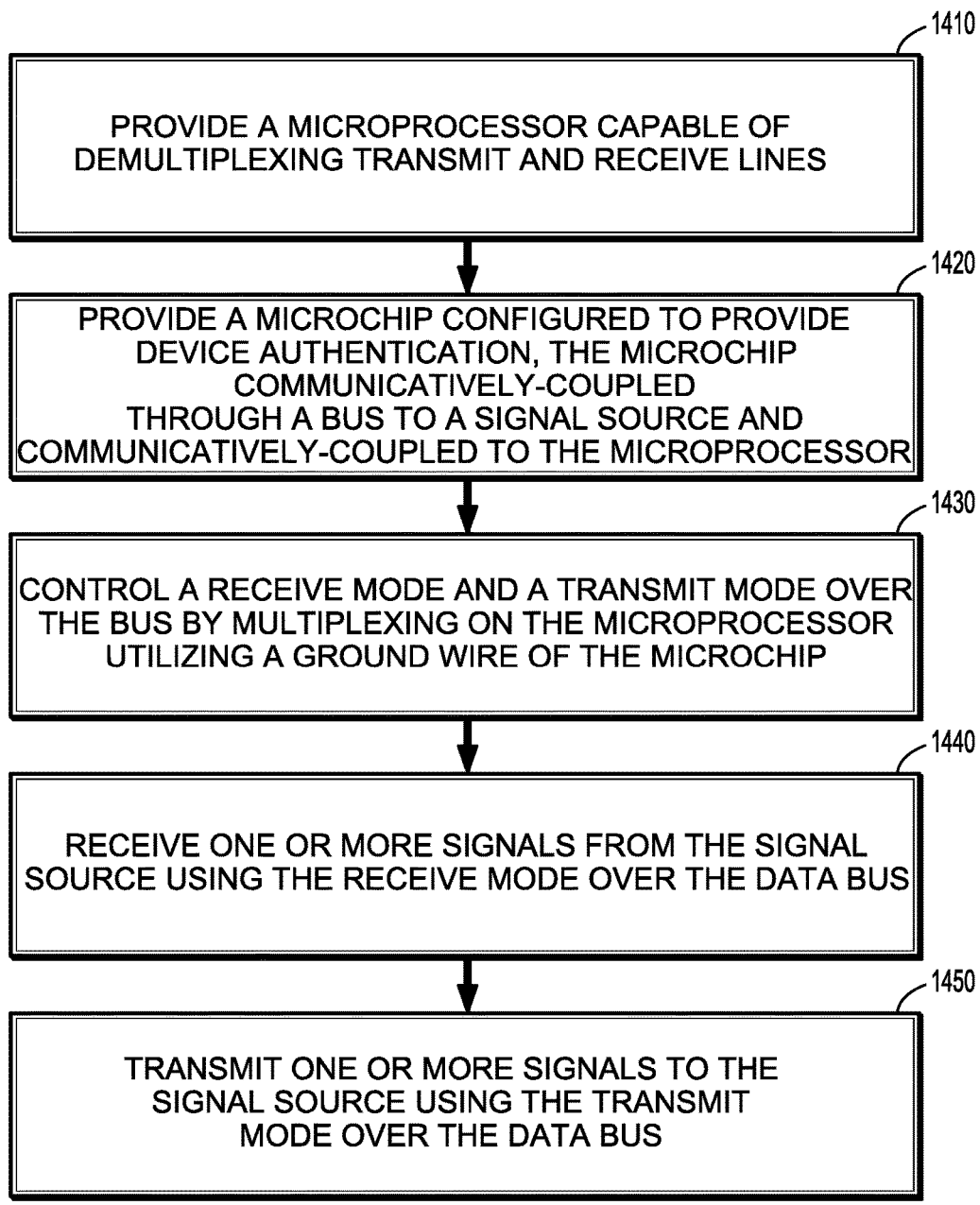
FIG. 61 is a flowchart illustrating a method of communicating data through a bus in accordance with an embodiment of the present disclosure.

FIG. 61 is a flowchart illustrating a method of communicating data through a bus in accordance with an embodiment of the present disclosure. In step 1410, a microprocessor 1020 capable of demultiplexing transmit and receive lines is provided.

In step 1420, a microchip 1030 configured to provide device authentication is provided. Microchip 1030 is communicatively-coupled through a bus 1010 to a signal source 1120 and communicatively-coupled to the microprocessor 1020. Microchip 1030 may utilize a one-wire data interface. The signal source transmits to microchip 1030 the combined data from microchips in the surgical system, such as for example the loading unit, staple cartridge assembly, and/or adapter.

In step 1430, a receive mode and a transmit mode over the bus 1010 are controlled by multiplexing on the microprocessor 1020 utilizing a ground wire 1012 of the microchip 1030.

In step 1440, at least one signal is received from the signal source 1120 using the receive mode over the bus 1010. In some embodiments, receiving at least one signal from the signal source 1120 using the receive mode over the bus 1010 includes turning on the ground wire 1012 of the microchip 1030. Receiving at least one signal from the signal source 1120 using the receive mode over the bus 1010 may further include selecting the receive mode utilizing the microprocessor 1020.

In step 1450, at least one signal is transmitted from the signal source 1120 using the transmit mode over the bus 1010. In some embodiments, transmitting at least one signal from the signal source 1120 using the transmit mode over the bus 10 includes turning off the ground wire 1012 of the microchip 1030. Transmitting at least one signal from the signal source 1120 using the transmit mode over the bus 1010 may further include selecting the transmit mode utilizing the microprocessor 1020.

In another embodiment of a method of communicating data through a bus in accordance with the present disclosure, the method includes: authenticating a surgical device, or component of a surgical system utilizing a microchip 1030 communicatively-coupled through a bus 1010 to a signal source 1120 and communicatively-coupled to a microprocessor 1020 capable of demultiplexing transmit and receive lines; and controlling a receive mode and a transmit mode over the bus 1010 by multiplexing on the microprocessor 1020 utilizing a ground wire 1012 of the microchip 1030. Authenticating the surgical device may include utilizing a one-wire data interface of the microchip 1030.

Various embodiments of the above-described PCBs utilize a receive mode and a transmit mode over a bus which is controlled by multiplexing on a microprocessor utilizing a ground wire of a microchip configured to provide device authentication.

It is contemplated that the protocol and/or multiplexor can be used to reduce the bus to two wires instead of three or four, from four wires to three, etc., reducing the communication connectors or pins to two or three, respectively.

Figure 62:
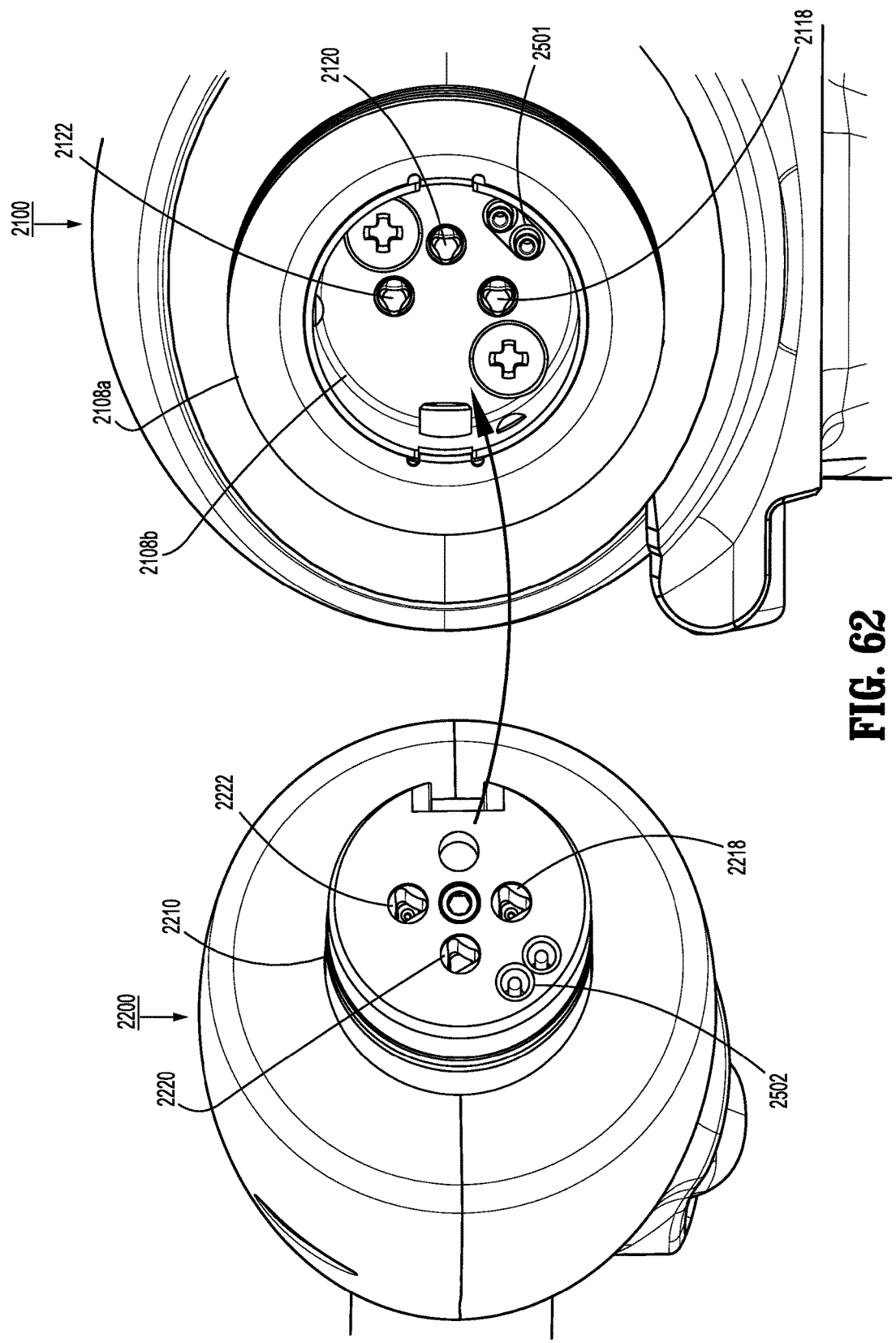
FIG. 62 is a perspective view of coupling assembly, shown de-coupled, and showing the rotatable drive connectors and communication connectors.

FIG. 62 is an exemplary coupling assembly for the surgical handle assembly 1100 and adapter assembly 1200, which can be used in any of the embodiments disclosed herein. A similar coupling assembly is provided between the adapter assembly and the loading unit. The connecting portion 2108a of surgical instrument 2100 has a cylindrical recess 2108b that receives a drive coupling assembly 2210 of adapter assembly 2200 when adapter assembly 2200 is mated to surgical instrument 2100. Connecting portion 2108a houses three rotatable drive connectors 2118, 2120, 2122.

When adapter 2200 is mated to surgical instrument 2100, each of rotatable drive connectors 2118, 2120, 2122 of surgical instrument 2100 couples with a corresponding rotatable connector sleeve 2218, 2220, 2222 of adapter 2200 as shown in FIG. 62. In this regard, the interface between corresponding first drive connector 2118 and first connector sleeve 2218, the interface between corresponding second drive connector 2120 and second connector sleeve 2220, and the interface between corresponding third drive connector 2122 and third connector sleeve 2222 are keyed such that rotation of each of drive connectors 2118, 2120, 2122 of surgical instrument 2100 causes a corresponding rotation of the corresponding connector sleeve 2218, 2220, 2222 of adapter assembly 2200.

The mating of drive connectors 2118, 2120, 2122 of surgical instrument 2100 with connector sleeves 2218, 2220, 2222 of adapter assembly 2200 allows rotational forces to be independently transmitted via each of the three respective connector interfaces. The drive connectors 2118, 2120, 2122 of surgical instrument 2100 are configured to be independently rotated by drive mechanism 2160. In this regard, the controller in the instrument or handle assembly 2100 selects which drive connector or connectors 2118, 2120, 2122 of surgical instrument 2100 is to be driven by a drive mechanism in the handle assembly or surgical instrument.

Each of drive connectors 2118, 2120, 2122 of surgical instrument 2100 has a keyed and/or substantially non-rotatable interface with respective connector sleeves 2218, 2220, 2222. The selective rotation of drive connector(s) 2118, 2120 and/or 2122 of surgical instrument 2100 allows surgical instrument 2100 to selectively actuate different functions of end effector/loading unit, such as loading unit 1300. Such functions include selective and independent opening and closing of tool assembly of loading unit such as loading unit 1300, driving of stapling and/or cutting, articulation of a tool assembly of a loading unit, and/or rotation of shaft 1302 and or shaft of the adapter assembly about a longitudinal axis thereof.

The coupling assembly also has communication connectors 2501 and 2502, which are shown in a pair in FIG. 62. In embodiments using the multiplexing scheme and/or multiplexor discussed above, signals from three chips (e.g., staple cartridge chip, loading unit chip, and adapter assembly chip) can be combined and communicated to a microprocessor (such as the one shown in FIG. 60). The controller of the surgical system can then use the data from such chips as discussed above. In certain preferred embodiments the communication connectors are singular connectors instead of the pair shown. In any of the embodiments disclosed herein, there may also be force and/or load sensors that connect to the microprocessor. In any of the embodiments disclosed herein the microprocessor such as microprocessor 1020 can transmit data to the one or more chips (staple cartridge chip, loading unit chip, and/or adapter assembly chip). Such data can include an indication that the staples have been fired, and/or incrementing a counter for the number of uses of the particular component. Such data can include the maximum drive force experienced and/or the position of the drive assembly/drive beam, etc.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A method of authenticating first and second components of a surgical system, the method comprising:
   receiving a first authentication signal of a first component from a first microchip at a second microchip over a single wire bus of the second microchip which interconnects the first and second microchips;
   switching a ground wire of the second microchip OFF with a microprocessor to select a transmit mode of the second microchip after receiving the first authentication signal, the microprocessor interconnected with the second microchip via a second bus and the ground wire; and
   transmitting a first data signal from the second microchip to the first microchip over the single wire bus after switching the ground wire OFF.

2. The method according to claim 1, wherein receiving the first authentication signal from the first microchip includes receiving the first authentication signal at the microprocessor over the second bus.

3. The method according to claim 2, wherein transmitting the second authentication signal includes the microprocessor transmitting the second authentication signal to the second microchip over the second bus.

4. The method according to claim 1, further comprising transmitting and receiving signals between the second microchip and the microprocessor over the second bus.

5. The method according to claim 4, wherein the microprocessor multiplexes signals over the second bus.

6. The method according to claim 1, further comprising switching the ground wire ON with the microprocessor to select a receive mode of the second microchip.

7. The method according to claim 6, wherein switching the ground wire ON occurs after transmitting the second authentication signal.

8. The method according to claim 7, further comprising receiving a second authentication signal from the first microchip at the second microchip over the single wire bus.

9. The method according to claim 8, further comprising switching the ground wire OFF and transmitting a second data signal from the second microchip to the first microchip after receiving the second authentication signal.

10. The method according to claim 9, wherein the first authentication signal is from a first component in communication with the first microchip and the second authentication signal is from a second component in communication with the first microchip.

11. The method according to claim 1, further comprising receiving a second authentication signal from a third microchip at the second microchip, the second and third microchips interconnected by the single wire bus of the second microchip.

12. A surgical system, comprising:
   a handle assembly;
   an adapter assembly releaseably coupled to the handle assembly;
   a loading unit having a tool assembly;
   a loading unit chip disposed within the loading unit, the loading unit chip storing data indicative of one or more properties of the tool assembly; and
   a controller disposed within the handle assembly and storing a program, the controller including a microprocessor in communication with the loading unit chip over a single wire bus, the microprocessor including a ground wire and configured to switch the loading unit chip between a receive mode and a transmit mode by switching the ground wire between ON and OFF positions33.

13. The surgical system according to claim 12, wherein the microprocessor is configured to multiplex data from the loading unit chip.

14. The surgical system according to claim 12, wherein the controller includes a controller chip connected to the microprocessor via a second bus and the ground wire and in communication with the loading unit chip over the single wire bus.

15. The surgical system according to claim 14, wherein the microprocessor is configured to switch the controller chip between a receive mode and a transmit mode by switching the ground wire between ON and OFF positions.

16. The surgical system according to claim 14, wherein the second bus is a one-wire bus.

17. The surgical system according to claim 12, wherein the one or more properties of the tool assembly includes whether the tool assembly is articulable relative to the loading unit.

18. The surgical system according to claim 17, wherein the controller reads the data and prevents actuation of an articulation link in the adapter assembly and/or loading unit if the data indicates that the tool assembly is not articulatable.

19. The surgical system according to claim 12, wherein the adapter includes an adapter chip in communication with the microprocessor over the single wire bus, the adapter chip storing data indicative of one or more properties of the adapter.

20. The surgical system according to claim 19, wherein the microprocessor is configured to switch the adapter chip between a receive mode and a transmit mode by switching the ground wire between ON and OFF positions.

* * * * *